US009057097B2

(12) United States Patent
Piepenburg et al.

(10) Patent No.: US 9,057,097 B2
(45) Date of Patent: *Jun. 16, 2015

(54) RECOMBINASE POLYMERASE AMPLIFICATION REAGENTS AND KITS

(75) Inventors: Olaf Piepenburg, Essex (GB); Niall A. Armes, Suffolk (GB)

(73) Assignee: Alere San Diego Inc., San Diego, CA (US)

( * ) Notice: Subject to any disclaimer, the term of this patent is extended or adjusted under 35 U.S.C. 154(b) by 585 days.

This patent is subject to a terminal disclaimer.

(21) Appl. No.: 13/375,264

(22) PCT Filed: Jun. 7, 2010

(86) PCT No.: PCT/US2010/037611
§ 371 (c)(1),
(2), (4) Date: Feb. 9, 2012

(87) PCT Pub. No.: WO2010/141940
PCT Pub. Date: Dec. 9, 2010

(65) Prior Publication Data
US 2012/0129173 A1    May 24, 2012

Related U.S. Application Data

(60) Provisional application No. 61/184,397, filed on Jun. 5, 2009.

(51) Int. Cl.
C12Q 1/68 (2006.01)
(52) U.S. Cl.
CPC ............ *C12Q 1/6806* (2013.01); *C12Q 1/6848* (2013.01)
(58) Field of Classification Search
USPC ....................................... 435/6.12, 91.1, 91.2
See application file for complete search history.

(56) References Cited

U.S. PATENT DOCUMENTS

| | | | |
|---|---|---|---|
| 4,683,195 A | 7/1987 | Mullis et al. | |
| 4,965,188 A | 10/1990 | Mullis et al. | |
| 5,223,414 A | 6/1993 | Zarling et al. | |
| 5,273,881 A | 12/1993 | Sena et al. | |
| 5,326,692 A | 7/1994 | Brinkley et al. | |
| 5,354,668 A | 10/1994 | Auerbach | |
| 5,418,149 A | 5/1995 | Gelfand et al. | |
| 5,430,136 A | 7/1995 | Urdea et al. | |
| 5,455,166 A | 10/1995 | Walker | |
| 5,536,649 A | 7/1996 | Fraiser et al. | |
| 5,556,751 A | 9/1996 | Stefano | |
| 5,591,609 A | 1/1997 | Auerbach | |
| 5,614,389 A | 3/1997 | Auerbach | |
| 5,656,430 A | 8/1997 | Chirikjian | |
| 5,665,572 A | 9/1997 | Ikeda et al. | |
| 5,670,316 A | 9/1997 | Sena et al. | |
| 5,705,366 A | 1/1998 | Backus | |
| 5,712,124 A | 1/1998 | Walker | |
| 5,731,150 A | 3/1998 | Sandhu et al. | |
| 5,733,733 A | 3/1998 | Auerbach | |
| 5,744,311 A | 4/1998 | Fraiser et al. | |
| 5,792,607 A | 8/1998 | Backman et al. | |
| 5,834,202 A | 11/1998 | Auerbach | |
| 5,849,547 A | 12/1998 | Cleuziat | |
| 5,858,652 A | 1/1999 | Laffler et al. | |
| 5,916,779 A | 6/1999 | Pearson et al. | |
| 5,942,391 A | 8/1999 | Zhang et al. | |
| 6,087,112 A | 7/2000 | Dale | |
| 6,165,793 A | 12/2000 | Stemmer | |
| 6,251,600 B1 | 6/2001 | Winger et al. | |
| 6,379,899 B1 | 4/2002 | Ullmann | |
| 6,387,621 B1 | 5/2002 | Wittwer | |
| 6,448,065 B2 | 9/2002 | Laugharn, Jr. et al. | |
| 6,566,103 B2 | 5/2003 | Wijnhoven et al. | |
| 6,699,693 B1 | 3/2004 | Marians et al. | |
| 6,929,915 B2 | 8/2005 | Benkovic et al. | |
| 7,112,423 B2 | 9/2006 | Van Ness et al. | |
| 7,252,940 B2 | 8/2007 | Kutyavin et al. | |
| 7,270,981 B2 | 9/2007 | Armes et al. | |
| 7,282,328 B2 | 10/2007 | Kong | |
| 7,399,590 B2 | 7/2008 | Piepenburg et al. | |
| 7,435,561 B2 | 10/2008 | Piepenburg et al. | |
| 7,485,428 B2 | 2/2009 | Armes et al. | |
| 7,666,598 B2 | 2/2010 | Piepenburg et al. | |

(Continued)

FOREIGN PATENT DOCUMENTS

| | | |
|---|---|---|
| CA | 2444649 | 10/2002 |
| CA | 2476481 | 9/2003 |

(Continued)

OTHER PUBLICATIONS

Gill et al., "Nucleic acid isothermal amplification technologies: a review," Nucleosides Nucleotides Nucleic Acids 2008 27:224-243.
Mukai et al., "Highly efficient isothermal DNA amplification system using three elements of 5'-DNA-RNA-3' chimeric primers, RNaseH and strand-displacing DNA polymerase," 2007, J. Biochem. 142:273-281.
Tan et al., "Isothermal DNA amplification coupled with DNA nanosphere-based colorimetric detection," Anal. Chem. 2005, 77:7984-7992.
Lizard et al., Nature Biotech. 1998, 6:1197-1202.
Mori et al., "Loop-mediated isothermal amplification (LAMP): a rapid, accurate, and cost-effective diagnostic method for infectious diseases," J. Infect. Chemother. 2009 15:62-69.
Kurn et al., "Novel isothermal, linear nucleic acid amplification systems for highly multiplexed applications," Clin. Chem. 2005, 51:10, 1973-1981.
Piekarowicz et al., "Characterization of the dsDNA prophage sequences in the genome of *Neisseria gonorrhoeae* and visualization of productive bacteriophage," 2007, BMC Microbiol., 7:66.

(Continued)

*Primary Examiner* — Kenneth R. Horlick
*Assistant Examiner* — Joyce Tung
(74) *Attorney, Agent, or Firm* — Fish & Richardson P.C.

(57) ABSTRACT

This disclosure describes kits, reagents and methods for Recombinase Polymerase Amplification (RPA) of a target DNA that exploit the properties of recombinase and related proteins, to invade double-stranded DNA with single stranded homologous DNA permitting sequence specific priming of DNA polymerase reactions. The disclosed kits, reagents and methods have the advantage of not requiring thermocycling or thermophilic enzymes, thus offering easy and affordable implementation and portability relative to other amplification methods.

41 Claims, 4 Drawing Sheets

(56) References Cited

U.S. PATENT DOCUMENTS

| | | | |
|---|---|---|---|
| 7,763,427 B2 | 7/2010 | Piepenburg et al. | |
| 7,777,958 B2 | 8/2010 | Shimmo et al. | |
| 8,017,339 B2 | 9/2011 | Piepenburg et al. | |
| 8,030,000 B2 | 10/2011 | Piepenburg et al. | |
| 8,062,850 B2 | 11/2011 | Piepenburg et al. | |
| 8,071,308 B2 | 12/2011 | Piepenburg et al. | |
| 8,426,134 B2* | 4/2013 | Piepenburg et al. | 435/6.12 |
| 8,574,846 B2* | 11/2013 | Piepenburg et al. | 435/6.12 |
| 2001/0044111 A1 | 11/2001 | Carr et al. | |
| 2002/0061530 A1 | 5/2002 | Belotserkovskii et al. | |
| 2002/0155573 A1 | 10/2002 | Lanes et al. | |
| 2003/0082565 A1 | 5/2003 | Jang | |
| 2003/0082590 A1 | 5/2003 | Van Ness et al. | |
| 2003/0108936 A1 | 6/2003 | Wagner | |
| 2003/0138800 A1 | 7/2003 | Van Ness et al. | |
| 2003/0143525 A1 | 7/2003 | Benkovic et al. | |
| 2003/0219792 A1 | 11/2003 | Armes et al. | |
| 2003/0228611 A1 | 12/2003 | Chruch et al. | |
| 2004/0038213 A1 | 2/2004 | Kwon | |
| 2004/0058378 A1 | 3/2004 | Kong et al. | |
| 2004/0101893 A1 | 5/2004 | Kutyavin et al. | |
| 2004/0137456 A1 | 7/2004 | Yokota et al. | |
| 2004/0224336 A1 | 11/2004 | Wagner | |
| 2005/0003395 A1 | 1/2005 | Gellibolian et al. | |
| 2005/0059003 A1 | 3/2005 | Enoki et al. | |
| 2005/0112631 A1 | 5/2005 | Piepenburg et al. | |
| 2005/0136443 A1 | 6/2005 | Shigemori | |
| 2006/0110765 A1 | 5/2006 | Wang | |
| 2006/0154286 A1 | 7/2006 | Kong et al. | |
| 2007/0054296 A1 | 3/2007 | Piepenburg et al. | |
| 2007/0154914 A1 | 7/2007 | Gelfand et al. | |
| 2007/0259348 A1* | 11/2007 | Phadke et al. | 435/6 |
| 2008/0076160 A1 | 3/2008 | Armes et al. | |
| 2008/0293045 A1 | 11/2008 | Piepenburg et al. | |
| 2009/0017453 A1 | 1/2009 | Maples et al. | |
| 2009/0017462 A1 | 1/2009 | Piepenburg et al. | |
| 2009/0029421 A1 | 1/2009 | Piepenburg et al. | |
| 2009/0081670 A1 | 3/2009 | Maples et al. | |
| 2009/0269813 A1 | 10/2009 | Piepenburg et al. | |
| 2009/0325165 A1 | 12/2009 | Armes et al. | |
| 2010/0234245 A1 | 9/2010 | McGee et al. | |
| 2010/0311127 A1 | 12/2010 | Piepenburg et al. | |
| 2011/0053153 A1 | 3/2011 | Piepenburg et al. | |
| 2011/0059506 A1 | 3/2011 | Piepenburg et al. | |
| 2011/0065106 A1 | 3/2011 | Armes et al. | |
| 2012/0015367 A1 | 1/2012 | Piepenburg et al. | |
| 2012/0021462 A1 | 1/2012 | Armes et al. | |
| 2012/0058517 A1 | 3/2012 | Piepenburg et al. | |
| 2012/0082990 A1 | 4/2012 | Piepenburg et al. | |
| 2012/0129173 A1 | 5/2012 | Piepenburg et al. | |
| 2014/0099674 A1* | 4/2014 | Piepenburg et al. | 435/91.2 |
| 2014/0234846 A1* | 8/2014 | Piepenburg et al. | 435/6.12 |

FOREIGN PATENT DOCUMENTS

| | | |
|---|---|---|
| EP | 0 624 643 | 4/1994 |
| EP | 0 702 090 | 3/1996 |
| EP | 0 810 436 | 12/1997 |
| EP | 1 420 069 | 5/2004 |
| EP | 1 564 306 | 8/2005 |
| JP | 08-103300 | 4/1996 |
| JP | 2000-500981 | 2/2000 |
| JP | 2008-515447 | 5/2008 |
| JP | 2009-502161 | 1/2009 |
| WO | WO 91/17267 | 11/1991 |
| WO | WO 93/05178 | 3/1993 |
| WO | WO 97/20078 | 6/1997 |
| WO | WO 98/08975 | 3/1998 |
| WO | WO99/60158 | 11/1999 |
| WO | WO 00/41524 | 7/2000 |
| WO | WO 00/46408 | 8/2000 |
| WO | WO 02/086167 | 10/2002 |
| WO | WO 03/027640 | 4/2003 |
| WO | WO 03/038053 | 5/2003 |
| WO | WO 03/072805 | 9/2003 |
| WO | WO 2004/007078 | 1/2004 |
| WO | WO 2004/027025 | 4/2004 |
| WO | WO 04/090169 | 10/2004 |
| WO | WO 2005/118853 | 12/2005 |
| WO | WO2006/040187 | 4/2006 |
| WO | WO 2007/096702 | 8/2007 |
| WO | WO2010141940 | 12/2010 |
| WO | WO 2013185081 | 12/2013 |

OTHER PUBLICATIONS

Liu et al., 2005, "Rapid identification of *Streptococcus pyogenes* with PCR primers from a putative transcriptional regulator gene," Res. Microbiol., 156:564-567.

Podbielski et al., "Molecular characterization of the cfb gene encoding group B streptococcal CAMP-factor," 1994, Med. Microbiol. Immunol., 183:239-256.

Schoenmakers et al., 1992, Biotechniques, 12:870-874.

Fujishiro et al., 1995, Comput. Biol. Med., 25:61-80.

Bahador et al., 2005, Res. J. Agr. Biol. Sci. 1;142-145.

International Search Report and Written Opinion in corresponding Application No. PCT/US13/44796, dated Nov. 8, 2013, pp. 1.

El-Harakany AA et al., "Dissociation Constants and Related Thermodynamic Quantities of The Protonated Acid Form of Tris-(Hydroxymethyl)-Aminomethane In Mixtures of 2-Methoxyethanol and Water At Different Temperatures," Journal of Electroanalytical Chemistry:162:285-305 & 296 (1984).

Granholm K. et al., "Desorption of Metal Ions from Kraft Pulps. Part 1. Chelation of Hardwood and Softwood Kraft Pulp With EDTA," Bioresources:5(1)206-226 (2010).

Office action in corresponding Canadian application 2,476,481, dated May 16, 2013, 9 pages.

Kim and Chae, "Optimized protocols for the detection of porcine circovirus 2 DNA from formalin-fixed paraffin-embedded tissues using nested polymerase chain reaction and comparison of nested PCR with in situ hybridization," J. Vir. Methods, 92:105-111, 2001.

Miyamoto et al., "Development of a New Seminested PCR Method for Detection of *Legionella* Species and Its Application to Surveillance of Legionellae in Hospital Cooling Tower Water," Applied and Environmental Microbiology, 63(7):2489-2494, 1997.

Monis and Saint, "Development of a Nested-PCR Assay for the Detection of Cryptosporidium Parvum in Finished Water," Wat. Res., 35(7):1641-1648, 2001.

Ozbas et al., "Development of a multiplex and semi-nested PCR assay for detection of *Yersinia enterocolitica* and *Aeromonas hydrophila* in raw milk," Food Microbiology, 17:197-203, 2000.

European Search Report for corresponding EP Application No. 10784225.4, dated Oct. 26, 2012.

Barnes and Rowlyk, "Magnesium precipitate hot start method for PCR," Mol. And Cell. Probes, 16(3):167-171, 2002.

Crowe et al., "Is Trehalose Special for Preserving Dry Biomaterials?," Biophys. J., 71(4):2087-2093, 1996.

Mannarelli and Kurtzman, "Rapid Identification of *Candida albicans* and Other Human Pathogenic Yeasts by Using Short Oligonucleotides in a PCR," J. Clin. Microbiol., 36(6):1634-1641, 1998.

Ramos et al., "Stabilization of Enzymes against Thermal Stress and Freeze-Drying by Mannosylglycerate," Appl. and Env. Microbiol., 63(10):4020-4025, 1997.

Accession: NP_861734 [GI: 32453528], Definition: UvsX RecA-like recombination protein [Enterobacteria phage RB69]. NCBI Sequence Revision History [online]; Mar. 30, 2006 uploaded, NCBI, <URL: http://www.ncbi.nlm.nih.gov/protein/32453528?sat=12&satkey=7706006> [retrieved on Aug. 30, 2011].

Accession: NP_861890 [GI: 32453681], Definition: UvsY recombination, repair and ssDNA binding protein [Enterobacteria phage RB69]. NCBI Sequence Revision History [online]; Mar. 30, 2006 uploaded, NCBI, <URL: http://www.ncbi.nlm.nih.gov/protein/32453681?sat=12&satkey=7706006> [retrieved on Aug. 30, 2011].

Adams et al., "Dissociation of RecA filaments from duplex DNA by the RuvA and RuvB DNA repair proteins," Proc. Natl. Acad. Sci. USA 91:9901-9905, 1994.

Alexseyev et al., "Genetic Characteristics of New *recA* Mutants of *Escherichia coli* K-12," J. Bacteriol., 178:2018-2024, 1996.

(56) References Cited

OTHER PUBLICATIONS

Amasino, "Acceleration of Nucleic Acid Hybridization Rate by Polyethylene Glycol," Anal. Biochem., 152:304-307, 1986.
Bains and Smith, "A Novel Method for Nucleic Acid Sequence Determination," J. Theor. Biol., 135:303-307, 1988.
Bar-Ziv and Libchaber, "Effects of DNA sequence and structure on binding of RecA to single-stranded DNA," PNAS USA, 98(16):9068-9073.
Baumann et al., "Purification of human Rad51 protein by selective spermidine precipitation," Mutat. Res., 384:65-72, 1997.
Benedict and Kowalczykowski, "Increase of the DNA Strand Assimiliation Activity of recA Protein by Removal of the C Terminus and Structure-Function Studies of the Resulting Protein Fragment," J. Biol. Chem., 263(30):15513-15520, 1988.
Benkovic et al., "Replisome-Mediated DNA Replication," Annu. Rev. Biochem., 70:181-208, 2001.
Bennett and Holloman, "A RecA Homologue in Ustilago maydis That Is Distinct and Evolutionarily Distant from Rad51 Actively Promotes DNA Pairing Reactions in the Absence of Auxiliary Factors," Biochemistry, 40:2942-2953, 2001.
Better and Helinski, "Isolation and Characterization of the recA Gene of Rhizobium meliloti," J. Bacteriol, 155:311-316, 1983.
Bianco and Weinstock, "Interaction of the RecA protein of *Escherichia coli* with single-stranded oligodeoxyribonucleotides," Nucleic Acids Research, 24(24):4933-4939, 1996.
Bianco et al., "DNA Strand Exchange Proteins: A Biochemical and Physical Comparison," Frontiers in Bioscience, 3:D570-D603, 1998.
Borjac-Natour et al., "Divergence of the mRNA targets for the Ssb proteins of bacteriophages T4 and RB69," Virology J., 1(4):1-14, 2004.
Bork et al., "The RecOR proteins modulate RecA protein function at 5' ends of single-stranded DNA," EMBO J., 20:7313-7322, 2001.
Bork et al., "RecA Protein Filaments Disassemble in the 5' to 3' Direction on Single-stranded DNA," J. Biol. Chem., 276:45740-45743, 2001.
Butler et al., "Investigating Structural Changes Induced by nucleotide Binding to RecA Using Difference FTIR," Biophysical J., 82(4):2198-2210, 2002.
Byrd and Raney, "Protein displacement by an assembly of helicase molecules aligned along single-stranded DNA," Nat. Struct. Mol. Biol., 11(6):531-538, 2004.
Cai, "An inexpensive and simple nucleic acid dipstick for rapid pathogen detection," LAUR #05-9067 of Los Alamos National Laboratory, Aug. 22, 2006.
Chan et al., "Effects of Polyethylene Glycol on Reverse Transcriptase and Other polymerase Activities," Biochim. Biophys. Acta., 606(2):353-361, 1980.
Compton, "Nucleic acid sequence-based amplification," Nature, 350:91-92, 1991.
Conklin and Drake, "Isolation and Characterization of conditional Alleles of bacteriophage T4 Genes uvsX and uvsY," Genetics, 107:505-523, 1984.
Cox et al., "The importance of repairing stalled replication forks," Nature, 404:37-41, 2000.
Cox et al., "A Simple and Rapid Procedure for the Large Scale Purification of the recA protein of *Escherichia coli*," J. Biol. Chem., 256:4676-4678, 1981.
Cromie and Leach, "Control of Crossing Over," Mol. Cell., 6:815-826. 2000.
Decker et al., "In Vitro Initiation of DNA Replication in Simian Virus 40 Chromosomes," J. Biol. Chem., 262(22):10863-10872, 1987.
Demidov, "Rolling-circle amplification in DNA diagnostics: the power of simplicity," Expert Rev. Mol. Diagn., 2(6):89-95, 2002.
Digard et al., "The Extreme C Terminus of Herpes Simplex Virus DNA Polymerase Is Crucial for Functional Interaction with Processivity Factor UL42 and for Viral Replication," J. Virol., 67(1):398-406, 1993.
Dillingham and Kowalczykowski, "A Step Backward in Advancing DNA Replication: Rescue of Stalled Replication Forks by RecG," Mol. Cell., 8:734-736, 2001.

Dong et al., "A coupled complex of T4 DNA replication helicase (gp41) and polymerase (gp43) can perform rapid and processive DNA strand-displacement synthesis," Proc. Natl. Acad. Sci. USA, 93:14456-14461, 1996.
Drmanac, et al., "Sequencing of Megabase Plus DNA by Hybridization: Theory of the Method," Genomics, 4:114-128, 1989.
Edwards et al., "Genetic Variation at Five Trimeric and Tetrameric Tandem Repeat Loci in Four Human Population Groups," Genomics, 12:241-253, 1992.
Eggler et al., "The C Terminus of the *Escherichia coli* RecA Protein Modulates the DNA Binding Competition with Single-stranded DNA-binding Protein," J. Biol. Chem., 278:16389-16396, 2003.
Eggleston and West, "Cleavage of Holliday Junctions by the *Escherichia coli* RuvABC Complex," J. Biol. Chem., 275:26467-26476, 2000.
Elias-Arnanz and Salas, "Bacteriophage ø29 DNA replication arrest caused by codirectional collisions with the transcription machinery," EMBO J., 16:5775-5783, 1997.
Ellis, "Macromolecular crowding: obvious but underappreciated," Trends in Biochem. Sci., 26(10):597-604, 2001.
Ellouze et al., "Evidence for elongation of the helical pitch of the RecA filament upon ATP and ADP binding using small-angle neutron scattering," Eur. J. Biochem., 23392):579-583, 1995.
Enright et al., The evolutionary history of methicillin-resistant *Staphylococcus aureus* (MRSA), Proc. Natl. Acad. Sci. USA, 99:7687-7692, 2002.
Fahy et al., "Self-sustained sequence replication (3SR): an isothermal transcription-based amplification system alternative to PCR," Genome Res, 1:25-33, 1991.
Ferrari et al., "Co-operative Binding of *Escherichia Coli* SSB Tetramers to Single-stranded DNA in the $(SSB)_{35}$ Binding Mode," J. Mol. Biol, 236:106-123, 1994.
Formosa et al., "Affinity purification of bacteriophage T4 proteins essential for DNA replication and genetic recombination," Proc. Natl. Acad. Sci. USA, 80:2442-2446, 1983.
Formosa and Alberts, "Purification and Characterization of the T4 Bacteriophage uvsX Protein," J. Biol. Chem., 261:6107-6118, 1986.
Formosa and Alberts, "DNA Synthesis Dependent on Genetic Recombination: Characterization of a Reaction Catalyzed by Purified Bacteriophage T4 Proteins," Cell, 47:793-806, 1986.
Fu et al., "Dynamics of DNA-tracking by two sliding-clamp proteins," EMBO J., 15(16):4414-4422, 1996.
Fuller et al., "Enzymatic replication of the origin of the *Escherichia coli* chromosome," Proc. Natl. Acad. Sci. USA, 78(12):7370-7374, 1981.
Giedroc et al., "The Function of Zinc in Gene 32 Protein from T4," Biochem., 26:5251-5259, 1987.
Giedroc et al., "Zn(II) Coordination Domain Mutants of T4 Gene 32 protein," Biochem., 31:765-774, 1992.
Ginocchio, "Life Beyond PCR: Alternative Target Amplification Technologies for the Diagnosis of Infectious Diseases, Part II," Clin. Microbiol. Newsletter, 26(17):129-136, 2004.
Glover and McHenry, "The DNA Polymerase III Holoenzyme: An Asymmetric Dimeric Replicative Complex with Leading and Lagging Strand Polymerases," Cell., 105:925-934.
Goodman et al., "Cloning and expression in *Escherichia coli* of a recA-like gene from *Bacteroides fragilis*," Gene, 58:265-271, 1987.
Hacker and Alberts, "Overexpression, Purification, Sequence Analysis, and Characterization of the T4 Bacteriophage dda DNA Helicase," J. Biol. Chem., 267:20674-20681, 1992.
Hammond et al., "Evaluation of 13 Short Tandem Repeat Loci for Use in Personal Identification Applications," Am. J. Hum. Genetics, 55:175-189, 1994.
Harris and Griffith, "UvsY Protein of Bacteriophage T4 is an Accessory Protein for in Vitro Catalysis of Strand Exchange," J. Mol. Biol., 206:19-27, 1989.
Harris and Griffith, "Visualization of the Homologous Pairing of DNA Catalyzed by the Bacteriophage T4 UvsX Protein," J. Biol. Chem., 262:9285-9292, 1987.
Harris and Griffith, "Formation of D Loops by the UvsX Protein of T4 Bacteriophage: A Comparison of the Reaction Catalyzed in the Presence or Absence of Gene 32 Protein," Biochem., 27:6954-6959, 1988.

(56) References Cited

OTHER PUBLICATIONS

Harvey et al., "Characterization and applications of CataCleave probe in real-time detection assays," Anal. Biochem., 333(2):246-255, 2004.
Heid et al., "Real time quantitative PCR," Genome Res., 6(10):986-994, 1996.
Heyer and Kolodner, "Purification and Characteirzation of a Protein from *Saccharomyces cerevisiae* That Binds Tightly to Single-Stranded DNA and Stimulates a cognate Strand Exchange Protein," Biochem. 28:2856-2862, 1989.
Hickson et al., "A Temperature Sensitive RecA Protein of *Escherichia coli*," Mol. Gen. Genet., 184:68-72, 1981.
Hopp et al., "A Short Polypeptide Marker Sequence Useful for Recombinant Protein Identification and Purification," Biotech., 6:1204-1210, 1988.
Hsieh et al., "The synapsis event in the homologous pairing of DNAs: RecA recognizes and pairs less than one helical repeat of DNA," Proc. Natl. Acad. Sci. USA, 89:6492-6496, 1992.
Huang et al., "Relationship between Bacteriophage T4 and T6 DNA Topoisomerases," J. Biol. Chem., 260(15):8973-8977, 1985.
Huletsky et al., "New Real-Time PCR Assay for Rapid Detection of Methicillin-Resistant *Staphylococcus aureus* Directly from Specimens Containing a Mixturre of Staphylococci," J. Clin. Microbiol., 42:1875-1884, 2004.
Ischenko and Saparbaev, "Alternative nucleotide incision repair pathway for oxidative DNA damage," Nature, 415(6868):183-187, 2002.
Ishmael et al., "Protein-Protein Interactions in the Bacteriophage T4 Replisome," J. Biol. Chem., 278(5):3145-3152, 2003.
Jarvis et al., "'Macromolecular Crowding': Thermodynamic Consequences for Protein-Protein Interactions with in the T4 DNA Replication Complex," J. Biol. Chem., 265(25):15160-15167, 1990.
Kaboord and Benkovic, "Rapid assembly of the bacteriophage T4 core replication complex on a linear primer/template construct," Proc. Natl. Acad. Sci. USA, 90:10881-10885, 1993.
Kaiser et al., "A Comparison of Eubacterial and Archaeal Structure-specific 5'-Exonucleases," J. Biol. Chem., 274(30):21387-21394, 1999.
Kato and Kuramitsu, "RecA Protein from an Extremely Thermophilic Bacterium, *Thermus thermophiles* HB8," J. Biochem., 114:926-929, 1993.
Katz and Bryant, "Interdependence of the Kinetics of NTP Hydrolysis and the Stability of the RecA-ssDNA Complex," Biochem., 40:11082-11089, 2001.
Kelman and O'Donnell, "DNA Polymerase III Holoenzyme: Structure and Function of a Chromosomal Replicating Machine," Annu. Rev. Biochem., 64:171-2000.
Khrapko et al., "An oligonucleotide hybridization approach to DNA sequencing," FEBS Lett., 256:118-122, 1989.
Komori et al., "Both RadA and RadB Are Involved in Homologous Recombination in *Pyrococcus furiosus*," J. Biol. Chem., 275:33782-33790, 2000.
Kool, "Replacing the Nucleobases in DNA with Designer Molecules," Acc. Chem. Res., 35:936-943, 2002.
Kowalczykowski et al., "Effects of the *Escherichia coli* SSB Protein on the Binding of *Escherichia coli* RecA Protein to Single-stranded DNA—Demonstration of Competitive Binding and the Lack of a Specific Protein-Protein Interaction," J. Mol. Biol., 193:81-95, 1987.
Kreader, "Relief of amplification inhibition in PCR with bovine serum albumin or T4 gene 32 protein," Appl. Env. Microbiol., 62:1102-1106, 1996.
Kuil et al., "The internal dynamics of gene 32 protein-DNA complexes studied by quasi-elastic light scattering," Biophys. Chem., 32:211-227, 1988.
Kuil et al., "A Refined Calculation of the Solution Dimensions of the Complex Between gene 32 Protein and Single Stranded DNA Based on Estimates of the Bending Persistence Length," J. Biomol. Struct. Dyn. 7(4):943-957, 1990.
Kuramitsu et al., "A Large-Scale Preparation and Some Physicochemical Properties of RecA Protein," J. Biochem., 90:1033-1045, 1981.
Kurumizaka et al., "A Chimeric RecA Protein Exhibits Altered Double-stranded DNA Binding," J. Biol. Chem., 269:3068-3075, 1994.
Lavery and Kowalczykowski, "Enhancement of recA Protein-promoted DNA Strand Exchange Activity by Volume-occupying Agents," J. Biol. Chem., 267:9301-9314, 1992.
Lavery and Kowalczykowski, "A Postsynaptic Role for Single-stranded DNA-binding Protein in recA Protein-promoted DNA Strand Exchange," J. Biol. Chem., 267(13):9315-9320, 1992.
LeBowitz and McMacken, "The bacteriophage λO and P protein initiators promote the replication of single-stranded DNA," 12(7):1-20, 1984.
Lerman, "A Transition to a Compact Form of DNA in Polymer Solutions," Proc. Nat. Acad. Sci. USA, 68(8):1886-1890, 1971.
Levin et al., "Homogeneous *Escherichia coli* Endonuclease IV," J. Biol. Chem., 263:8066-8071, 1988.
Liu et al., "The Ordered Assembly of the øX174-type Primosome," J. Biol. Chem., 271:15656-15661, 1996.
Lohman and Ferrari, "*Escherichia Coli* Single-Stranded DNA-Binding Protein: Multiple DNA-Binding Modes and Cooperativities," Annu. Rev. Biochem., 63:527-570, 1994.
Lovett and Roberts, "Purification of a RecA Protein Analogue from *Bacillus subtilis*," J. Biol. Chem., 260:3305-3313, 1985.
Lusetti et al., "Magnesium Ion-dependent Activation of the RecA Protein Involves the C Terminus," J. Biol. Chem., 278(18):16381-16388, 2003.
Lutz-Freyermuth et al., "Quantitative determination that one of two potential RNA-binding domains of the A protein component of the U1 small nuclear ribonucleoprotein complex binds with high affinity to stem-loop II of U1 RNA," Proc. Natl. Acad. Sci. USA, 87:6393-6397, 1990.
Lysov et al., "Establishing Nucleotide Sequence of DNA using Oligonucleotide Hydridization. Novel Method," SSSR 303:1508-1511, 1988 (English translation).
Maeshima et al., "Purification and characterization of XRad51.1 protein, Xenopus RAD51 homologue: recombinant XRad51.1 promotes strand exchange reaction," Genes Cells, 1:1057-1068, 1996.
Maki et al., "DNA Polymerase III Holoenzyme of *Escherichia coli*," J. Biol. Chem., 263(14):6570-6578, 1988.
Malkov and Camerini-Otero, Photocross-links between Single-stranded DNA and *Escherichia coli* RecA Protein Map to Loops L1 (Amino Acid Residues 157-164) and L2 (Amino Acid Residues 195-209),: J. Biol. Chem., 270(50):30230-30233, 1995.
Marians, "Prokaryotic DNA Replication," Annu. Rev. Biochem., 61:673-719, 1992.
Marians, "PriA: At the Crossroads of DNA Replication and Recombination," Prog. Nucleic Acid Res. Mol. Biol., 63:39-67, 1999.
Marras et al., "Multiplex detection of single-nucleotide variations using molecular beacons," Genet. Anal. Biomolec. Eng., 14:151-156, 1999.
Martin et al., "GAP Domains Responsible for Ras p21-Dependent Inhibition of Muscarinic Atrial $K^+$channel Currents," Science, 255:192-194, 1992.
Maxam and Gilbert, "A new method for sequencing DNA," Proc. Natl. Acad. Sci. USA, 74:560-564, 1877.
Mazin and Kowalczykowski, "The function of the secondary DNA-binding site of RecA protein during DNA strand exchange," Proc. Natl. Acad. Sci. USA, 74:560-564, 1977.
McGlynn and Lloyd, "RecG helicase activity at three- and four-strand DNA structures," Nucl. Acid Res., 27:3049-3056, 1999.
McGlynn et al., "Characterisation of the catalytically active form of RecG helicase," Nucl. Acid Res., 28:2324-2332, 2000.
Minton, "The Influence of Macromolecular Crowding and Macromolecular Confinement on Biochemical Reactions in Physiological Media," J. Biol. Chem., 276(14):10577-10580, 2001.
Mitra and Church, "In situ localized amplification and contact replication of many individual DNA molecules," Nucl. Acids Res., 27(24):e34i-e34vi.
Mizuuchi, "In Vitro Transposition of Bacteriophage Mu: A Biochemical Approach to a Novel Replication Reaction," Cell, 35:785-794, 1983.

(56) References Cited

OTHER PUBLICATIONS

Morel et al., "Recombination-dependent Repair of DNA Double-strand Breaks with Purified Proteins from *Escherichia coli*," J. Biol. Chem., 272:17091-17096, 1997.
Morrical et al., "Amplification of Snap-back DNA Synthesis Reactions by the uvsX Recombinase of Bacteriophage T4," J. Biol. Chem., 266:14031-14038, 1991.
Morrical and Alberts, "The UvsY Protein of Bacteriophage T4 Modulates Recombination-dependent DNA Synthesis in Vitro," J. Biol. Chem., 265:15096-15103, 1990.
Morris and Raney, "DNA Helicases Displace Streptavidin from Biotin-Labeled Oligonucleotides," Biochem., 38(16):5164-5171, 1999.
Morrison et al., "Quantificationo f Low-Copy Transcripts by Continuous SYBR Green I Monitoring during Amplification," BioTechniques, 24:954-962, 1998.
Mosig et al., "Two recombination-dependent DNA replication pathways of bacteriophage T4, and their roles in mutagenesis and horizontal gene transfer," Proc. Natl. Acad. Sci. USA, 98:8306-8311, 2011.
Nadler et al., "A Novel Function for Zinc(II) in a Nucleic Acid-binding Protein," J. Biol. Chem., 265(18):10389-10394, 1990.
Nadeau et al., "Real-Time, Sequence-Specific Detection of Nucleic Acids during Strand Displacement Amplification," Anal. Biochem., 276(2):177-187, 1999.
Nagai et al., "Additive Effects of Bovine Serum Albumin, Dithiothreitol, and Glycerol in PCR," 44:157-163, 1998.
Naimushin et al., "Effect of Polyethylene Glycol on the Supercoiling Free Energy of DNA," Biopolymers, 58(2):204-217, 2001.
Ng and Marians, "The Ordered Assembly of the øX174-type Primosome," J. Biol. Chem., 271:15642-15648, 1996.
Ng and Marians, "The Ordered Assembly of the øX174-type Primosome," J. Biol. Chem., 271:15649-15655, 1996.
Okazaki and Kornberg, "Enzymatic Synthesis of Deoxyribonucleic Acid," J. Biol. Chem., 239:259-268, 1964.
Paulus and Bryant, "Time-Dependent Inhibition of recA Protein-Catalyzed ATPHydrolysis by ATPγS: Evidence for a Rate-Determining Isomerization of the recA-ssDNA Complex," Biochem., 36:7832-7838, 1997.
Petrov et al., "Plasticity of the Gene Functions for DNA Replication in the T4-like Phages," J. Mol. Biol., 361:46-68, 2006.
Pevzner, "1-Tuple DNA Sequencing: Computer Analysis," J. Biomol. Struct. Dyn., 7:63-73, 1989.
Pham et al., "A model for SOS-lesion-targeted mutations in *Escherichia coli*," Nature, 409:366-370, 2001.
Piepenburg et al., "DNA Detection Using Recombination Proteins," PLOS Biology, 4(7):1115-1121, 2006.
Pierre and Paoletti, "Purification and Characterization of recA Protein from *Salmonella typhimurium*," J. Biol. Chem., 258:2870-2874, 1983.
Podust et al., "Replication Factor C Disengages from Proliferating Cell Nuclear Antigen (PCNA) upon Sliding Clamp Formation, and PCNA Itself Tethers DNA Polymerase δ to DNA," J. Biol. Chem., 273(48):31992-31999, 1998.
Pomp and Medrano, "Organic Solvents as Facilitators of Polymerase chain Reaction," Biotechniques, 10(1):58-59, 1991.
Qiu and Giedroc, "Effects of Substitution of Proposed Zn(II) Ligand His$^{81}$ or His$^{64}$ in Phage T4 Gene 32 Protein: Spectroscopic Evidence for a Novel Zinc Coordination Complex," Biochem., 33(26):8139-8148, 1994.
Raap, "Advances in fluorescence in situ hybridization," Mutation Research, 400:287-298, 1998.
Raap et al., "Synthesis and Proton-NMR Studies of Oligonucleotides Containing and Apurinic (AP) Site," J. Biom. Structure & Dynamics, 5(2):219-247, 1987.
Rashid et al., "RecA/Rad51 Homolog from *Thermococcus kodakaraensis* KOD1," Methods Enzymol., 334:261-270, 2001.

Reddy et al., "Assembly of a functional replication complex without ATP hydrolysis: A direct interaction of bacteriophage T4 gp45 with T4 DNA polymerase," Proc. Natl. Acad. Sci. USA, 90:3211-3215, 1993.
Reddy et al., "Using Macromolecular Crowding Agents to Identify Weak Interactions within DNA Replication Complexes," Methods Enzymol., 262:466-476, 1995.
Riddles and Lehman, "The Formation of Plectonemic Joints by the recA Protein of *Escherichia coli*," J. Biol. Chem., 260:170-173, 1985.
Rivas et al., "Life in a crowded world—Workshop on the Biological Implications of Macromolecular Crowding," EMBO Reports, 5(1):23-27, 2004.
Ronaghi et al., "A Sequencing Method Based on Real-Time Pyrophosphate," Science, 281:363-365, 1998.
Rosselli and Stasiak, "Energetics of RecA-mediated Recombination Reactions Without ATP Hydrolysis RecA Can Mediate Polar Strand Exchange But Is Unable to Recycle," J. Mol. Biol., 216:335-352, 1990.
Roux, "Optimization and troubleshooting in PCR," Genome Res., 4:S185-S194, 1995.
Saiki et al., "Primer-Directed Enzymatic Amplification of DNA with a Thermostable DNA Polymerase," Science, 239:487-491, 1988.
Salinas et al., "Homology Dependence of UvsX Protein-catalyzed Joint Molecule Formation," J. Biol. Chem., 270:5181-5186.
Salinas and Benkovic, "Characterization of bacteriophage T4-coordinated leading- and lagging-strand synthesis on a minicircle substrate," PNAS, 97(13):7196-7201, 2000.
Sanders et al., "Use of a macromolecular crowding agent to dissect interactions and define functions in transcriptional activation by a DNA-tracking protein: Bacteriphage T4 gene 45 protein and late transcription," Proc. Natl. Acad. Sci. USA, 91:7703-7707, 1994.
Sanders et al., "Dual targets of a transcriptional activator that tracks on DNA," EMBO J., 16(11):3124-3132, 1997.
Sanger et al., "DNA sequencing with chain-terminating inhibitors," Proc. Natl. Acad. Sci. USA, 75:5463-5467, 1977.
Savva and Pearl, "Cloning and Expression of the Uracil-DNA Glycosylase Inhibitor (UGI) From Bacteriophage PBS-1 and Crystallization of a Uracil-DNA Glycosylase-UGI Complex," Proteins, 22(3):287-289, 1995.
Scheerhagen et al., "Binding Stoichiometry of the Gene 32 Protein of Phage T4 in the Complex with Single Stranded DNA Deduced from Boundary Sedimentation," J. Biomol. Struct. Dyn., 3:887-898, 1986.
Scheerhagen et al., "Hydrodynamic studies of a DNA-protein complex—Dimensions of the complex of single-stranded 145 base DNA with gene 32 protein of phage T4 deduced from quasi-elastic light scattering," FEBS Lett., 184(2):221-225, 1985.
Shan et al., "RecA Protein Filaments: End-dependent Dissociation from ssDNA and Stabilization by RecO and RecR Proteins," J. Mol. Biol., 265:519-540, 1997.
Shibata et al., "Purified *Escherichia coli* recA protein catalyzes homologous pairing of superhelical DNA and single-stranded fragments," Proc. Natl. Acad. Sci. USA, 76:1638-1642, 1979.
Shibata et al., "Homologous pairing in genetic recombination: Formation of D loops by combined action of recA protein and a helix-destabilizing protein," Proc. Natl. Acad. Sci. USA, 77:2606-2610, 1980.
Shibata et al, "Homologous pairing in genetic recombination: Complexes of recA protein and DNA," Proc. Natl. Acad. Sci. USA, 76(10):5100-5104, 1979.
Singleton et al., "Structural Analysis of DNA Replication Fork Reversal by RecG," Cell, 107:79-89, 2001.
Skinner et al., "Use of the Glu-Glu-Phe C-terminal Epitope for Rapid Purification of the Catalytic Domain of Normal and Mutant ras GTPase-activating Proteins," J. Biol. Chem., 266:14163-14166, 1991.
Southern et al., "Analyzing and Comparing Nucleic Acid sequences by Hybridization to Arrays of Oligonucleotides: Evaluation Using Experimental Models," Genomics, 13:1008-1017, 1992.
Spies et al., "The RadA protein from a hyperthermophilic archaeon *Pyrobaculum islandicum* is a DNA-dependent ATPase that exhibits two disparate catalytic modes, with a transition temperature at 75° C," Eur. J. Biochem., 267:1125-1137, 2000.

(56) References Cited

OTHER PUBLICATIONS

Steffen and Bryant, "Purification and Characterization of the RecA Protein from *Streptococcus pneumoniae*," Arch. Biochem. Biophys., 382:303-309, 2000.
Story et al., "Structural Relationship of Bacterial RecA Proteins to Recombination Proteins from Bacteriophage T4 and Yeast," Science, 259(5103):1892-1896, 1993.
Sun and Shamoo, "Biochemical characterization of Interactions between DNA Polymerase and Single-stranded DNA-binding Protein in Bacteriophage RB69," J. Biol. Chem., 278(6):3876-3881.
Takeshita et al., "Oligodeoxynucleotides Containing Synthetic Abasic Sites," J. Biol. Chem., 262:10171-10179, 1987.
Tang et al., "Roles of *E. coli*DNA polymerases IV and V in lesion-targeted and untargeted SOS mutagenesis," Nature, 404:1014-1018, 2000.
Tinker-Kulberg et al., "A direct interaction between a DNA-tracking protein and a promoter recognition protein: implications for searching DNA sequence," EMBO J., 15(18):5032-5039, 1996.
Tissier et al., "Purification and Characterization of a DNA Strand Transferase from Broccoli," Plant Physiol., 108:379-386, 1995.
Tracy and Kowalczykowski, "In vitro selection of preferred DNA pairing sequences by the *Escherichia coli* RecA protein," Genes Dev., 10:1890-1903, 1996.
Tsurimoto and Matsubara, "Replication of λ dv plasmid in vitro promoted by purified λ O and P proteins," Proc. Natl. Acad. Sci. USA, 79:7639-7643, 1982.
Tyagi et al., "Multicolor molecular beacons for allele discrimination," Nature Biotechnol., 16:49-53, 1998.
Van Ness et al., "Isothermal reactions for the amplification of oligonucleotides," Proc. Natl. Acad. Sci. USA, 100(8):4504-4509, 2003.
Villemain et al., "Mutations in the N-terminal Cooperativity Domain of Gene 32 protein Alter Properties of the T4 DNA Replication and Recombination Systems," J. Biol. Chem., 275:31496-31504, 2000.
Vincent et al., "Helicase-dependent isothermal DNA amplification," EMBO Rep., 5:795-800, 2004.
Volodin and Camerini-Otero, "Influence of DNA Sequence on the Positioning of RecA Monomers in RecA-DNA Cofilaments," J. Biol. Chem., 277(2):1614-1618, 2002.
Volodin et al., "Phasing of RecA monomers on quasi-random DNA sequences," FEBS Letters, 546:203-208, 2003.
Voloshin et al., "Homologous DNA Pairing Promoted by a 20-Amino Acid Peptide Derived from RecA," Science, 272:868-872, 1996.
Voloshin et al., "The Homologous Pairing Domain of RecA also Mediates the Allosteric Regulation of DNA Binding and ATP Hydrolysis: A Remarkable Concentration of Functional Residues," J. Mol. Biol., 303(5):709-720, 2000.
Waidner, et al., "Domain effects on the DNA-interactive properties of bacteriophage T4 gene 32 protein," J. Biol. Chem., 276:2509-16 (2001).
Walker et al., "Isothermal in vitro amplification of DNA by a restriction enzyme/DNA polymerase system," Proc. Natl. Acad. Sci. USA, 89:392-396, 1992.
Walker, "Empirical aspects of strand displacement amplification," Genome Res., 3:1-6, 1993.
Walker et al., "Distantly related sequences in the α- and β-subunits of ATP synthase, myosin, kinases and other ATP-requiring enzymes and a common nucleotide binding fold," EMBO J., 1:945-951, 1982.
Wang et al., "Modular Organization of T4 DNA Polymerase," J. Biol. Chem., 270(44):26558-26564, 1995.
Wang and Mosbaugh, "Uracil-DNA Glycosylase Inhibitor of Bacteriophage PBS2: Cloning and Effects of Expression of the Inhibitor Gene in *Escherichia coli*," J. Bacteriol., 170(3):1082-1091, 1988.
Webb et al., "An Interaction between the *Escherichia coli* RecF and RecR Proteins Dependent on ATP and Double-stranded DNA," J. Biol. Chem., 270:31397-31404, 1995.
Webb et al., "Recombinational DNA Repair: The RecF and RecR Proteins Limit the Extension of RecA Filaments beyond Single-Strand DNA Gaps," Cell, 91:347-356, 1997.
Webb et al., "ATP Hydrolysis and DNA Binding by the *Escherichia coli* RecF Protein," J. Biol. Chem., 274:15367-15374, 1999.
West et al., "Purification and Properties of the recA Protein of *Proteus mirabilis*," J. Biol. Chem., 258:4648-4654, 1983.
Wetmur et al, "Cloning, Sequencing, and Expressiono f RecA Proteins from Three Distantly Related Thermophilic Eubacteria," J. Biol. Chem., 269:25928-25935, 1994.
Wittwer et al., "Continuous Fluorescence Monitoring of Rapid Cycle DNA Amplification," Biotechniques, 22(1):130-1, 134-138, 1997.
Xu and Marians, "A Dynamic RecA Filament Permits DNA Polymerase-catalyzed Extension of the Invading Strand in Recombination Intermediates," J. Biol. Chem., 277:14321-14328, 2002.
Yang et al., "Comparison of Bacteriophage T4 and UvsX and Human Rad51 Filaments Suggests that RecA-like Polymers May Have Evolved Independently," J. Mol. Biol., 312(5):999-1009, 2001.
Yeh et al., "Divergence of a DNA Replication Gene Cluster in the T4-Related Bacteriophage RB69," J. Bacteriol., 180(8):2005-2013, 1998.
Yonesaki et al., "Purification and some of the functions of the product of bacteriophage T4 recombination genes, uvsX and uvsY ," Eur. J. Biochem., 148:127-134, 1985.
Young et al., "The Kinetic Mechanism of Formation of the Bacteriophage T4 DNA polymerase Sliding Clamp," J. Mol. Biol., 264:440-452, 1996.
Zhang et al., "Ramification Amplification: A Novel Isothermal DNA Amplification Method," Mol. Diagn., 6:141-150, 2001.
Zimmerman and Trach, "Macromolecular crowding extends the range of conditions under which DNA polymerase is functional," Biochim. Biophys. Acta., 949:297-304, 1988.
Zimmerman and Minton, "Macromolecular Crowding: Biochemical, Biophysical, and Physiological Consequences," Annu. Rev. Biophys. Biomol. Struct., 22:27-65, 1993.
Zimmerman and Harrison, "Macromolecular crowding increases binding of DNA polymerase to DNA: An adaptive effect," Proc. Natl. Acad. Sci. USA, 84(7):1871-1875, 1987.
Zinchenko and Yoshikawa, "Na$^+$ Shows a Markedly Higher Potential than K$^+$ in DNA Compaction in a Crowded Environment," Biophysical Journal, 88:4118-4123, 2005.
International Preliminary Report on Patentability for the corresponding PCT Application No. PCT/US2010/037611, dated Dec. 6, 2011.
Office Action in corresponding EP Application No. 10784225.4-1404, dated Feb. 5, 2014, pp. 1-5.
"UvsX RecA-like recombination protein [Enterobacteria phage RB69]", online NCBI, http://www.ncbi.nlm.nih.gov/protein/32350347?sat=13&satkey=7100722, Apr. 5, 2005 (retrieved on Aug. 22, 2012).
"UvsX [*Aeromonas* phage Aehl]", online NCBI, http://www.ncbi.nlm.nih.gov/protein/38639939?sat=12&satkey=851579, Mar. 30, 2006 (retrieved on Aug. 22, 2012).
Desplats and Krisch, "The diversity and evolution of the T4-type bacteriophages," Res. Microbiol, 154(4):259-267, 2003.
Miller et al., "Complete Genome Sequence of the Broad-Host-Range vibriophage KVP40: Comparative Genomics of a T4-Related Bacteriophage," J. Bacteriol., 185(17):5220-5233, 2003.
U.S. Appl. No. 10/371,641, filed Feb. 21, 2003, now U.S. Appl. No. 7,270,981, issued on Sep. 18, 2007.
U.S. Appl. No. 11/893,113, filed Aug. 13, 2007, now U.S. Appl. No. 7,485,428, issued on Feb. 3, 2009.
U.S. Appl. No. 12/322,354, filed Jan. 30, 2009 (abandoned).
U.S. Appl. No. 12/799,786, filed Apr. 30, 2010 (abandoned).
U.S. Appl. No. 13/192,806, filed Jul. 28, 2011 (pending).
U.S. Appl. No. 10/931,916, filed Sep. 1, 2004, now U.S. Appl. No. 7,399,590, issued on Jul. 15, 2008.
U.S. Appl. No. 12/151,741, filed May 7, 2008, now U.S. Appl. No. 7,763,427, issued on Jul. 27, 2010.
U.S. Appl. No. 12/802,862, filed Jun. 14, 2010, now U.S. Appl. No. 8,017,339, issued on Sep. 13, 2011.
U.S. Appl. No. 13/198,142, filed Aug. 4, 2011 (pending).
U.S. Appl. No. 11/628,179, filed Aug. 30, 2007, now U.S. Appl. No. 7,666,598, issued on Feb. 23, 2010.
U.S. Appl. No. 12/660,117, filed Feb. 19, 2010, now U.S. Appl. No. 8,030,000 issued on Oct. 4, 2011.
U.S. Appl. No. 13/212,361, filed Aug. 18, 2011 (pending).

(56) References Cited

OTHER PUBLICATIONS

U.S. Appl. No. 11/988,825, filed Jun. 2, 2009; now U.S. Appl. No. 8,062,850, issued on Nov. 22, 2011.
U.S. Appl. No. 11/493,677, filed Jul. 25, 2006; now U.S. Appl. No. 7,435,561, issued on Oct. 14, 2008.
U.S. Appl. No. 13/177,007, filed Jul. 6, 2011 (pending).
U.S. Appl. No. 11/800,318, filed May 4, 2007, now U.S. Appl. No. 8,071,308, issued on Dec. 6, 2011.
U.S. Appl. No. 13/307,293, filed Nov. 30, 2011 (pending); and.
U.S. Appl. No. 12/800,633, filed May 18, 2010 (pending).
Notice of Reasons for Rejection in corresponding Application No. JP2012-209422, dated Mar. 3, 2015, pp. 1-15.
Tetart et al., "Phylogeny of the Major Head and Tail Genes of the Wide-Ranging T4-Type Bacteriophages," Journal of Bacteriology, vol. 183(1):358-366 (2001).
Office Action in corresponding EP Application No. 10180482.1, dated May 30, 2014, pp. 1-5.
Response to the Article 94 in EP Application No. 11184367.8, dated Oct. 23, 2013, pp. 1-12.
Reddy et al., Joints Made by RecA Protein in the Interior of Linear Duplex DNA: Effects of Single-Stranded Ends, Length of Homology, and Dynamic State, *Biochemistry*, 33:11486-11492 (1994).
Toshihiro Horii et al., "Organization of the recA gene of *Escherichia coli*," Proc. Natl. Acad. Sci. USA., 77(1):313-317 (1980).
Examination Report from corresponding European Application No. 11184367.8-1403, dated Aug. 7, 2014, pp. 1-7.
Office Action from corresponding Japanese Application No. 2012-511958, dated Oct. 3, 2014, pp. 1-5.
English translation of Office Action from corresponding Japanese Application No. 2012-511958, dated Oct. 3, 2014, pp. 1-5.
Extended European Search Report in corresponding Application No. 14170595.4, dated Jan. 7, 2015, pp. 1-5.

* cited by examiner

RECOMBINASE POLYMERASE AMPLIFICATION REAGENTS AND KITS

RELATED APPLICATIONS

This application claims the benefit of priority to U.S. Provisional Patent Application No. 61/184,397 filed Jun. 5, 2009, which is hereby incorporated by reference in its entirety.

FIELD OF THE INVENTION

The present invention relates to reagents and kits, and the use of such reagents and kits, for the amplification of nucleic acids. More specifically, the present invention relates to the use of reagents and kits in recombinase polymerase amplification processes.

BACKGROUND OF THE INVENTION

Recombinase Polymerase Amplification (RPA) is a process in which recombinase-mediated targeting of oligonucleotides to DNA targets is coupled to DNA synthesis by a polymerase (U.S. Pat. No. 7,270,981 filed Feb. 21, 2003; U.S. Pat. No. 7,399,590 filed Sep. 1, 2004; U.S. Pat. No. 7,435,561 filed Jul. 25, 2006 and U.S. Pat. No. 7,485,428 filed Aug. 13, 2007, as well as, U.S. application Ser. No. 11/628,179, filed Aug. 30, 2007; Ser. No. 11/800,318 filed May 4, 2007 and 61/179,793 filed May 20, 2009; the disclosures of the foregoing patents and patent applications are each hereby incorporated by reference in its entirety). RPA depends upon components of the cellular DNA replication and repair machinery. The notion of employing some of this machinery for in vitro DNA amplification has existed for some time (Zarling et al., U.S. Pat. No. 5,223,414), however the concept has not transformed to a working technology until recently as, despite a long history of research in the area of recombinase function involving principally the *E. coli* RecA protein, in vitro conditions permitting sensitive amplification of DNA have only recently been determined (Piepenburg et al. U.S. Pat. No. 7,399,590, also Piepenburg et al., PlosBiology 2006). Development of a 'dynamic' recombination environment having adequate rates of both recombinase loading and unloading that maintains high levels of recombination activity for over an hour in the presence of polymerase activity proved technically challenging and needed specific crowding agents, notably PEG molecules of high molecular weight (e.g., Carbowax 20M molecular weight 15-20,000 and PEG molecular weight 35,000), in combination with the use of recombinase-loading factors, specific strand-displacing polymerases and a robust energy regeneration system.

The RPA technology depended critically on the empirical finding that high molecular weight polyethylene glycol species (particularly >10,000 Daltons or more) very profoundly influenced the reaction behavior. It has previously been discovered that polyethylene glycol species ranging in size from at least molecular weight 12,000 to 100,000 stimulate RPA reactions strongly. While it is unclear how crowding agents influence processes within an amplification reaction, a large variety of biochemical consequences are attributed to crowding agents and are probably key to their influence on RPA reactions.

Crowding agents have been reported to enhance the interaction of polymerase enzymes with DNA (Zimmerman and Harrison, 1987), to improve the activity of polymerases (Chan E. W. et al., 1980), to influence the kinetics of RecA binding to DNA in the presence of SSB (Lavery P E, Kowalczykowski S C. J Biol Chem. 1992 May 5; 267(13):9307-14).

Crowding agents are reported to have marked influence on systems in which co-operative binding of monomers is known to occur such as during rod and filament formation (Rivas et al., 2003) by increasing association constants by potentially several orders of magnitude (see Minton, 2001). In the RPA system multiple components rely on co-operative binding to nucleic acids, including the formation of SSB filaments, recombinase filaments, and possibly the condensation of loading agents such as UvsY. Crowding agents are also well known to enhance the hybridization of nucleic acids (Amasino, 1986), and this is a process that is also necessary within RPA reactions. Finally, and not least, PEG is known to drive the condensation of DNA molecules in which they change from elongated structures to compact globular or toroidal forms, thus mimicking structures more common in many in vivo contexts (see Lerman, 1971; also see Vasilevskaya. et. al., 1995; also see Zinchenko and Anatoly, 2005) and also to affect the supercoiling free energy of DNA (Naimushin et al., 2001).

Without intending to be bound by theory, it is likely that crowding agents influence the kinetics of multiple protein-protein, protein-nucleic acid, and nucleic acid-nucleic acid interactions within the reaction. The dependence on large molecular weight crowding agents for the most substantial reaction improvement (probably greater than about 10,000 Daltons in size) may reflect a need to restrict the crowding effect to reaction components over a certain size (for example oligonucleotides, oligonucleotide:protein filaments, duplex products, protein components) while permitting efficient diffusion of others (say nucleotides, smaller peptides such as UvsY). Further, it may also be that the high molecular weight preference might reflect findings elsewhere that as PEG molecular weight increases the concentration of metal ions required to promote DNA condensation decreases. In any case it is an empirical finding that RPA is made effective by the use of high molecular weight polyethylene glycols.

In addition to a need for specific type of 'crowded' reaction conditions as described above (reaction in the presence of crowding agents), effective RPA reaction kinetics depend on a high degree of 'dynamic' activity within the reaction with respect to recombinase-DNA interactions. In other words, the available data which includes (i) reaction inhibition by ATP-γ-S, or removal of the acidic C terminus of RecA or UvsX, and (ii) inhibition by excessive ATP (Piepenburg et al., 2006) suggest that not only is it important that recombinase filaments can be formed rapidly, but also important that they can disassemble quickly. This data is consistent with predictions made in earlier U.S. Pat. No. 7,270,981. Rapid filament formation ensures that at any given moment there will be a high steady state level of functional recombinase-DNA filaments, while rapid disassembly ensures that completed strand exchange complexes can be accessed by polymerases.

SUMMARY OF THE INVENTION

The invention provides a kit and reagents for, as well as methods of, DNA amplification, termed RPA. RPA comprises the following steps (See FIG. 1): First, a recombinase agent is contacted with a first and a second nucleic acid primer to form a first and a second nucleoprotein primer. Second, the first and second nucleoprotein primers are contacted to a double stranded target sequence to form a first double stranded structure at a first portion of said first strand and form a double stranded structure at a second portion of said second strand so the 3' ends of said first nucleic acid primer and said second nucleic acid primer are oriented towards each other on a given template DNA molecule. Third, the 3' end of said first and second nucleoprotein primers are extended by DNA polymerases to generate first and second double stranded nucleic acids, and first and second displaced strands of nucleic acid. Finally, the second and third steps are repeated until a desired degree of amplification is reached.

In one aspect, embodiments of the present invention provide compositions and kits for recombinase polymerase amplification processes of DNA amplification of a target nucleic acid molecule, which include one or more freeze dried pellets. For example, each freeze dried pellet includes a combination of the following reagents in the following concentrations (which unless otherwise indicated can be the concentration either when reconstituted or when freeze dried): (1) 1.5%-5% (weight/lyophilization mixture volume) of polyethylene glycol (e.g., 2.28% (weight/lyophilization mixture volume) of polyethylene glycol with a molecular weight of 35 kilodaltons); (2) 2.5%-7.5% weight/volume of trehalose (e.g., 5.7%); (3) 0-60 mM Tris buffer; (4) 1-10 mM DTT; (5) 150-400 µM dNTPs; (6) 1.5-3.5 mM ATP; (7) 100-350 ng/µL uvsX recombinase; (8) optionally 50-200 ng/µL uvsY; (9) 150-800 ng/µL gp32; (10) 30-150 ng/µL Bacillus subtilis Pol I (Bsu) polymerase or S. aureus Pol I large fragment (Sau polymerase); (11) 20-75 mM phosphocreatine; and (12) 10-200 ng/µL creatine kinase.

In another aspect, rehydration buffers for reconstituting freeze dried pellets for nucleic acid amplification are provided. In some embodiments, the rehydration buffer for reconstituting the freeze dried pellets are included with the kits described herein and, the rehydration buffer includes 0-60 mM Tris buffer, 50-150 mM Potassium Acetate, and 2.5%-7.5% weight/volume of polyethylene glycol. In certain embodiments, the kits further include a 160-320 mM Magnesium Acetate solution.

In certain embodiments of the compositions and kits described herein, the freeze dried pellets also include the first and/or the second nucleic acid primers for the RPA process. In certain embodiments of the foregoing kits, the freeze dried pellets also include a nuclease. For example, the nuclease is exonuclease III (exoIII), endonuclease IV (Nfo) or 8-oxoguanine DNA glycosylase (fpg).

In certain embodiments of the compositions and kits described herein, the kits or compositions may further include positive control primers and target DNA to test the activity of the kit components. For example, the kit can include a positive control DNA (e.g., human genomic DNA) and first and second primers specific for the positive control DNA.

In another aspect, methods of recombinase polymerase amplification are provided comprising the following steps: First, one of the kits or compositions described herein that include one or more freeze dried pellets and rehydration buffer is provided. Second, at least one of the freeze dried pellets is reconstituted, in any order, with the rehydration buffer, the first and the second nucleic acid primers for the RPA process, the target nucleic acid, and optionally water to a desired volume. Third, Magnesium (e.g., Magnesium Acetate solution) is added to initiate the reaction. Finally, the reaction is incubated until a desired degree of amplification is achieved. In some embodiments, this last step comprises mixing the sample several minutes after the reaction is initiated.

In yet another aspect, embodiments of the present invention also provide methods to control RPA reactions, achieved by initiating the RPA reaction with the addition of Magnesium (e.g., with Magnesium Acetate). For example, the methods include at least three steps. In the first step, the following reagents are combined in a solution in the absence of Magnesium: (1) at least one recombinase; (2) at least one single stranded DNA binding protein; (3) at least one DNA polymerase; (4) dNTPs or a mixture of dNTPs and ddNTPs; (5) a crowding agent (e.g., polyethylene glycol); (6) a buffer; (7) a reducing agent; (8) ATP or ATP analog; (9) optionally at least one recombinase loading protein; (10) a first primer and optionally a second primer; and (11) a target nucleic acid molecule. In the second step, Magnesium is added to initiate the reaction. In the third step, the reaction is incubated until a desired degree of amplification is achieved. In certain embodiments, one or more of the reagents are freeze dried before the first step.

In yet another aspect, embodiments of the present invention also include nucleic acid amplification mixtures for isothermal nucleic acid amplification. For example, the mixtures include at least: (1) at least one recombinase; (2) at least one single stranded DNA binding protein; (3) at least one strand displacing polymerase DNA polymerase; (4) dNTPs or a mixture of dNTPs and ddNTPs; (5) ATP or ATP analog; (6) trehalose; (7) optionally at least one recombinase loading protein; (8) optionally polyethylene glycol (9) optionally a first primer and optionally a second primer; and (10) optionally a target nucleic acid molecule.

In another aspect, embodiments of the present invention include kits for nucleic acid amplification processes, such as isothermal nucleic acid amplification processes (e.g., RPA amplification of DNA) a target nucleic acid molecule, which include one or more freeze dried pellets. In some embodiments, the freeze dried pellets comprise polyethylene glycol. For example, the amount of polyethylene glycol in the freeze dried pellets is an amount to allow the amplification process to proceed (0.3%-7.5% weight/lyophilization mixture volume of PEG). In some embodiments, the freeze dried pellets comprise trehalose. For example, the amount of trehalose in the freeze dried pellets is 2.5%-7.5% weight/lyophilization mixture volume of trehalose.

In yet another aspect, embodiments of the present invention include any of the freeze dried pellets described herein. In some embodiments, the freeze dried pellets comprise polyethylene glycol. For example, the amount of polyethylene glycol in the freeze dried pellets is an amount to allow the amplification process to proceed (0.3%-7.5% weight/lyophilization mixture volume of PEG). In some embodiments, the freeze dried pellets comprise trehalose. For example, the amount of trehalose in the freeze dried pellets is 2.5%-7.5% weight/lyophilization mixture volume of trehalose.

In yet another aspect, embodiments of the present invention include rehydration buffers for reconstituting the freeze dried pellets described herein. In some embodiments, the rehydration buffer comprises polyethylene glycol (e.g., 0.3%-7.5% weight/volume of PEG). In some embodiments, a kit comprising any of the foregoing rehydration buffers is provided.

Other embodiments, objects, aspects, features, and advantages of the invention will be apparent from the accompanying description and claims. It is contemplated that whenever appropriate, any embodiment of the present invention can be combined with one or more other embodiments of the present invention, even though the embodiments are described under different aspects of the present invention.

DETAILED DESCRIPTION OF THE INVENTION

Brief Description of RPA

Figure 1:
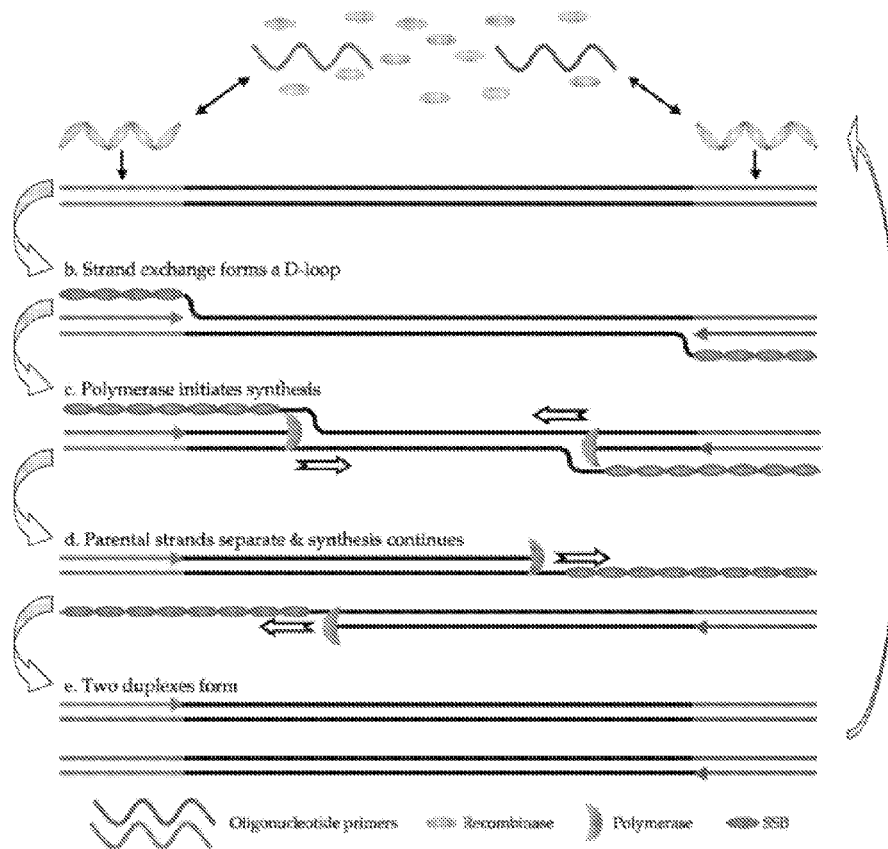
FIG. 1 schematically depicts an RPA reaction.

RPA is a method (process) for amplifying DNA fragments. RPA employs enzymes, known as recombinases, that are capable of pairing oligonucleotide primers with homologous sequence in duplex DNA. In this way, DNA synthesis is directed to defined points in a sample DNA. Using two gene-specific primers, an exponential amplification reaction is initiated if the target sequence is present. The reaction progresses rapidly and results in specific amplification from just a few target copies (such as less than 10,000 copies, less than 1000 copies, less than 100 copies or less than 10 copies) to detectable levels within as little as 20-40 minutes.

RPA reactions contain a blend of proteins and other factors that are required to support both the activity of the recombination element of the system, as well as those which support DNA synthesis from the 3' ends of oligonucleotides paired to complementary substrates. The key protein component of the recombination system is the recombinase itself, which may originate from prokaryotic, viral or eukaryotic origin. Additionally, however, there is a requirement for single-stranded DNA binding proteins to stabilize nucleic acids during the various exchange transactions that are ongoing in the reaction. A polymerase with strand-displacing character is required specifically as many substrates are still partially duplex in character. Reduction to practice has established that in order to make the reaction capable of amplifying from trace levels of nucleic acids precise in vitro conditions are required that include the use of crowding agents and loading proteins. A system comprising a bacteriophage T6 UvsX recombinase (e.g., T6UvsXH66S), a bacteriophage Rb69 UvsY loading agent, a bacteriophage Rb69 gp32 and a S. aureus Pol I large fragment has proven to be effective.

Embodiments of the present invention provide for Recombinase Polymerase Amplification (RPA)—a method for the amplification of target nucleic acid polymers. They also provide for a general in vitro environment in which high recombinase activity is maintained in a highly dynamic recombination environment, supported by ATP. One benefit of RPA is that it may be performed without the need for thermal melting of double-stranded templates. Therefore, the need for expensive thermocyclers is also eliminated.

Throughout this specification, various patents, published patent applications and scientific references are cited to describe the state and content of the art. Those disclosures, in their entireties, are hereby incorporated into the present specification by reference.

In Recombinase Polymerase Amplification single-stranded, or partially single-stranded, nucleic acid primers are targeted to homologous double-stranded, or partially double-stranded, sequences using recombinase agents, which form D-loop structures. The invading single-stranded primers, which are part of the D-loops, are used to initiate polymerase synthesis reactions. A single primer species will amplify a target nucleic acid sequence through multiple rounds of double-stranded invasion followed by synthesis. If two opposing primers are used, amplification of a fragment—the target sequence—can be achieved.

The target sequence to be amplified, in any of the embodiments of the present invention, is preferably a double stranded DNA. However, the embodiments of the present invention are not limited to double stranded DNA because other nucleic acid molecules, such as a single stranded DNA or RNA can be turned into double stranded DNA by one of skill in the art using known methods. Suitable double stranded target DNA may be a genomic DNA or a cDNA. An RPA of the invention may amplify a target nucleic acid at least 10 fold, preferably at least 100 fold, more preferably at least 1,000 fold, even more preferably at least 10,000 fold, and most preferably at least 1,000,000 fold.

The terms 'nucleic acid polymer' or 'nucleic acids' as used in this description can be interpreted broadly and include DNA and RNA as well as other hybridizing nucleic-acid-like molecules such as those with substituted backbones e.g. peptide nucleic acids (PNAs), morpholino backboned nucleic acids, locked nucleic acid or other nucleic acids with modified bases and sugars.

In addition, nucleic acids of embodiments of the present invention may be labeled with a detectable label. A detectable label includes, for example, a fluorochrome, an enzyme, a fluorescence quencher, an enzyme inhibitor, a radioactive label and a combination thereof.

Lyophilization of the RPA Reaction

One advantage of RPA is that the reagents for RPA, may be freeze dried (i.e., lyophilized) before use. Freeze dried reagents offer the advantage of not requiring refrigeration to maintain activity. For example, a tube of RPA reagents may be stored at room temperature. This advantage is especially useful in field conditions where access to refrigeration is limited. Freeze dried reagents also offer the advantage of long term storage without significant activity loss. For example, a tube of RPA reagents may be stored at −20° C. for up to six months without significant activity loss.

While lyophilization is a well-established process there is no guarantee that all components of a reaction system will successfully be co-lyophilized and reconstituted under the same conditions. We have attempted to lyophilize RPA reactions with and without various of the final reaction components. The disaccharide sugar trehalose proves in these experiments to be required to stabilize the lyophilisate, permitting room temperature storage for at least 10 days. We have also found that it is preferable to exclude the salt (e.g., Potassium Acetate) and reduce the buffer concentration to 25 mM of Tris or less from the lyophilisate, to maximize its stability—particularly for storage above 0° C.

We have also found that, if salt is present in the lyophilisate, polyethylene glycol is required to stabilize the lyophilisate. By contrast, if salt is not present, then PEG is not required to stabilize the lyophilizate, and need only be provided in the rehydration buffer. A typical RPA reaction will have a final PEG concentration in the reaction of 5%-6% (w/v).

In addition trehalose and PEG, the reagents that can be freeze dried before use can include, at least, the recombinase, the single stranded DNA binding protein, the DNA polymerase, the dNTPs or the mixture of dNTPs and ddNTPs, the reducing agent, the ATP or ATP analog, the recombinase loading protein, and the first primer and optionally a second primer or a combination of any of these.

In some embodiments, the RPA reagents may be freeze dried onto the bottom of a tube, or on a bead (or another type of solid support). In use, the reagents are reconstituted with buffer (a) Tris-Acetate buffer at a concentration of between 0 mM to 60 mM; (b) 50 mM to 150 mM Potassium Acetate and (c) polyethylene glycol at a concentration of between 2.5% to 7.5% by weight/volume. If the primers were not added before freeze drying, they can be added at this stage. Finally, a target nucleic acid, or a sample suspected of containing a target nucleic acid is added to begin the reaction. The target, or sample, nucleic acid may be contained within the reconstitution buffer as a consequence of earlier extraction or processing steps. The reaction is incubated until a desired degree of amplification is achieved.

We have found that it is possible to increase the sensitivity of the RPA reaction by agitating or mixing the sample several minutes (e.g., two, three, four, five or six minutes) after reconstituting and initiating the reaction. For example, after reconstituting and initiating the RPA reaction, the tube containing the RPA reaction is placed into an incubator block set to a temperature of 37° C. and is incubated for 4 minutes. The sample is then taken out of the incubator, vortexed and spun down. The sample is then returned to the incubator block and incubated for an additional 15-40 minutes.

In one aspect, embodiments of the present invention comprise kits for performing RPA reactions. In certain embodiments, the kits include one or more freeze dried pellets each including a combination of reagents for performing RPA reactions. In certain embodiments, the kits comprise 8 freeze dried pellets. In some embodiments, the kits comprise 96 freeze dried pellets. If desired, the freeze dried reagents may be stored for 1 day, 1 week, 1 month or 1 year or more before use.

In certain embodiments, the pellets can be assembled by combining each reagent in the following concentrations (which unless otherwise indicated can be the concentration either when reconstituted or when freeze dried): (1) 1.5%-5% (weight/lyophilization mixture volume) of polyethylene glycol; (2) 2.5%-7.5% weight/volume of trehalose; (3) 0-60 mM Tris buffer; (4) 1-10 mM DTT; (5) 150-400 µM dNTPs; (6) 1.5-3.5 mM ATP; (7) 100-350 ng/µL uvsX recombinase; (8) optionally 50-200 ng/µL uvsY; (9) 150-800 ng/µL gp32; (10) 30-150 ng/µL Bsu polymerase or Sau polymerase; (11) 20-75 mM phosphocreatine; and (12) 10-200 ng/µL creatine kinase. For example, the reagents in the solution mixture frozen for lyophilization can have approximately the following concentrations: (1) 2.28% weight/volume of polyethylene glycol with a molecular weight of 35 kilodaltons; (2) 5.7% weight/volume of trehalose; (3) 25 mM Tris buffer; (4) 5 mM DTT; (5) 240 µM dNTPs; (6) 2.5 mM ATP; (7) 260 ng/µL uvsX recombinase; (8) 88 ng/µL uvsY; (9) 254 ng/µL gp32; (10) 90 ng/µL Bsu polymerase or Sau polymerase; (11) 50 mM phosphocreatine; and (12) 100 ng/µL creatine kinase. The reagents may be freeze dried onto the bottom of a tube or in a well of a multi-well container. The reagents may be dried or attached onto a mobile solid support such as a bead or a strip, or a well.

While it is often preferred that the volume of the reagent mixture that is frozen and lyophilized is the same as the final volume of the RPA reaction after rehydration, this is not necessary. For example, an 80 µL volume of reagents can be freeze dried, which can then be reconstituted to a final RPA reaction volume of 50 µL.

In certain embodiments, the kits further include a rehydration buffer for reconstituting the freeze dried pellets, where the rehydration buffer includes 0-60 mM Tris buffer, 50-150 mM Potassium Acetate, and 0.3%-7.5% weight/volume of polyethylene glycol. For example, the rehydration buffer includes approximately 25 mM Tris buffer, 100 mM Potassium Acetate, and 5.46% weight/volume of polyethylene glycol with a molecular weight of 35 kilodaltons. In certain embodiments, the kit will comprise 4 mL of rehydration buffer.

In certain embodiments, the kits further include a 160-320 mM Magnesium Acetate solution (e.g., about 280 mM Magnesium Acetate solution). In some embodiments, the kit will comprise 250 µL of the Magnesium Acetate solution. In other embodiments, the rehydration buffer itself will comprise 8-16 mM Magnesium Acetate (e.g., about 14 mM Magnesium Acetate).

In certain embodiments of the foregoing kits, the freeze dried pellets also include the first and/or the second nucleic acid primers for the RPA process. In certain embodiments of the foregoing kits, the freeze dried pellets also include 50-200 ng/µL of either exonuclease III (exoIII), endonuclease IV (Nfo) or 8-oxoguanine DNA glycosylase (fpg).

In any of the foregoing embodiments, the kit may further include positive control primers and target DNA to test the activity of the kit components. For example, the kit can include a positive control DNA (e.g., human genomic DNA) and first and second primers specific for the positive control DNA.

In yet another aspect, embodiments of the present invention also include nucleic acid amplification mixtures for isothermal nucleic acid amplification. For example, the mixtures include at least: (1) at least one recombinase; (2) at least one single stranded DNA binding protein; (3) at least one strand displacing polymerase DNA polymerase; (4) dNTPs or a mixture of dNTPs and ddNTPs; (5) ATP or ATP analog; (6) trehalose; (7) optionally at least one recombinase loading protein; (8) optionally polyethylene glycol (9) optionally a first primer and optionally a second primer; and (10) optionally a target nucleic acid molecule.

In another aspect, embodiments of the present invention include kits for nucleic acid amplification processes, such as isothermal nucleic acid amplification processes (e.g., RPA amplification of DNA) a target nucleic acid molecule, which include one or more freeze dried pellets. In some embodiments, the freeze dried pellets comprise polyethylene glycol. For example, the amount of polyethylene glycol in the freeze dried pellets is an amount to allow the amplification process to proceed (0.3%-7.5% weight/lyophilization mixture volume of PEG). In some embodiments, the freeze dried pellets comprise trehalose. For example, the amount of trehalose in the freeze dried pellets is 2.5%-7.5% weight/lyophilization mixture volume of trehalose.

In yet another aspect, embodiments of the present invention include any of the freeze dried pellets described herein. In some embodiments, the freeze dried pellets comprise polyethylene glycol. For example, the amount of polyethylene glycol in the freeze dried pellets is an amount to allow the amplification process to proceed (0.3%-7.5% weight/lyophilization mixture volume of PEG). In some embodiments, the freeze dried pellets comprise trehalose. For example, the amount of trehalose in the freeze dried pellets is 2.5%-7.5% weight/lyophilization mixture volume of trehalose.

In yet another aspect, embodiments of the present invention include rehydration buffers for reconstituting the freeze dried pellets described herein. In some embodiments, the rehydration buffer comprises polyethylene glycol (e.g., 0.3%-7.5% weight/volume of PEG). In some embodiments, a kit comprising any of the foregoing rehydration buffers is provided.

RPA initiation by Magnesium

In another aspect, methods of recombinase polymerase amplification are provided comprising the following steps: First, one of the foregoing kits that include one or more freeze dried pellets and rehydration buffer is provided. Second, at least one of the freeze dried pellets is reconstituted, in any order, with the rehydration buffer, the first and the second nucleic acid primers for the RPA process, the target nucleic acid, and optionally water to a desired volume. Third, Magnesium (e.g., Magnesium Acetate solution) is added to initiate the reaction. Finally, the reaction is incubated until a desired degree of amplification is achieved.

RPA is a versatile method, but it can be improved by incorporation of features to control the RPA reaction. Embodiments of the present invention also provide methods to control RPA reactions, achieved by initiating the RPA reaction with the addition of Magnesium (e.g., with Magnesium Acetate). For example, the method includes at least three steps. In the first step, the following reagents are combined in a solution in the absence of Magnesium: (1) at least one recombinase; (2) at least one single stranded DNA binding protein; (3) at least one DNA polymerase; (4) dNTPs or a mixture of dNTPs and ddNTPs; (5) a crowding agent (e.g., polyethylene glycol); (6) a buffer; (7) a reducing agent; (8) ATP or ATP analog; (9) optionally at least one recombinase loading protein; (10) a first primer and optionally a second primer; and (11) a target nucleic acid molecule. In the second step, Magnesium is added to initiate the reaction. In the third step, the reaction is incubated until a desired degree of amplification is achieved. In certain embodiments, one or more of the reagents are freeze dried before the first step. Furthermore, it is possible to initiate a plurality of RPA reactions simultaneously by the simultaneous addition of Magnesium to each reaction.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Reagents for RPA Reactions

To form a freeze dried reaction pellet for a typical single basic RPA reaction, the following RPA reagents with the indicated concentrations are freeze dried (lyophilized) onto the bottom of a tube:

Basic RPA Freeze Dried Reaction Pellet

| Component | Concentration |
| --- | --- |
| PEG 35,000 | 2.28% (w/v) |
| Trehalose | 5.7% (w/v) |
| UvsX recombinase | 260 ng/µL |
| UvsY | 88 ng/µL |
| Gp32 | 254 ng/µL |
| Sau polymerase | 90 ng/µL |
| ATP | 2.5 mM |
| dNTPs | 240 µM |
| Tris buffer | 25 mM |
| DTT | 5 mM |
| Phosphocreatine | 50 mM |
| Creatine kinase | 100 ng/µL |

For reconstituting the freeze dried reaction pellet, a rehydration solution is prepared from the following rehydration buffer:

Rehydration Buffer

| Component | Concentration |
| --- | --- |
| Tris buffer | 25 mM |
| Potassium Acetate | 100 mM |
| PEG 35,000 | 5.46% (w/v) |

Unlike PCR, which requires small volumes for rapid temperature change, there is no limit to the reaction volume of RPA. Reaction volumes of 25 µL, 50 µL, 100 µL, 1 mL, 10 mL and 100 mL or larger may be performed in one vessel. For the examples given below, a reaction volume of 50 µL is used.

To permit monitoring of the RPA reaction, a nuclease may also be added to each freeze dried reaction pellet. For example, the "Exo RPA Freeze Dried Reaction Pellet" is the basic RPA freeze-dried reaction pellet plus 96 ng/µL exonuclease III (exoIII). Similarly, the "Nfo RPA Freeze Dried Reaction Pellet" is the basic RPA freeze-dried reaction pellet plus 62 ng/µL endonuclease IV (Nfo). Finally, the "Fpg RPA Freeze Dried Reaction Pellet" is the basic RPA freeze-dried reaction pellet plus 114 ng/µL 8-oxoguanine DNA glycosylase (fpg).

The tubes with the freeze dried pellets can be vacuum-sealed in pouches, for example in 12 strips of 8 pouches/strip for a total of 96 RPA reactions. While the vacuum-sealed pouches can be stored at room temperature for days without loss of activity, long term storage (up to at least about six months) at −20° C. is preferred. The rehydration buffer can be stored as frozen aliquots, for example 4×1.2 mL aliquots. For long term storage (up to at least about six months), storage at −20° C. is preferred. Unused rehydration buffer can be refrozen, or stored at 4° C. for up to 1 week. However, excessive freeze-thaw cycles should be avoided.

Example 2

Basic RPA Reaction

A basic RPA reaction for each sample is established by reconstituting the basic RPA freeze-dried reaction pellet of Example 1 with a suitable rehydration solution. The rehydration solution is prepared from the rehydration buffer of Example 1, amplification primers, and template (and water to a total volume of 47.5 µL per sample).

The components of the rehydration solution can be combined in a master-mix for the number of samples required. In some circumstances, for example when performing a primer screen, a number of different rehydration solutions are to be made (here according to the number of primer pairs being tested). In that case components common to all reactions (e.g., template, rehydration buffer, water) is prepared as a master-mix, distributed in a corresponding volume into fresh tubes, and is combined with the required volume of the different primer pairs. The different rehydration solutions are then used as normal according to the protocol below.

The reaction is initiated by the addition of 2.5 µL of a 280 mM Magnesium-Acetate solution, bringing the final reaction volume to 50 µL per sample.

For each sample, the rehydration solution is prepared by adding 2.4 µL of the first primer (10 µM), 2.4 µL of the second primer (10 µM), the Template and H₂O to a total volume of 18 µL. 29.5 ηL of the rehydration buffer of Example 1 is added. The rehydration solution is then vortexed and is spun briefly.

For each sample, the 47.5 µL of rehydration solution is transferred to a basic RPA freeze-dried reaction pellet of Example 1. The sample is mixed by pipetting up and down until the entire pellet has been resuspended.

For each sample, 2.5 µL of 280 mM Magnesium-Acetate is added and is mixed well. One way to do this simultaneously for many samples is to place the Magnesium-Acetate into the lid of the reaction tubes and then spin it down into the tubes to initiate the reactions. The reaction mixture is vortexed briefly and is spun down once again.

The tubes are place into a suitable incubator block (e.g., set to a temperature of 37-39° C.) and are incubated for 4 minutes. For ultra-high sensitivity, after 4 minutes, the samples are taken out of the incubator, vortexed, spun down and returned to the incubator block. The total incubation time is 20-40 minutes. If a timecourse of the reaction is desired the incubation time is adjusted as required. After the reaction is completed, the outcome of each reaction is typically analyzed by an endpoint method, such as agarose-gel-electrophoresis.

Example 3

Detection Probes for Use with RPA Reactions

A detection probe can be used to monitor RPA reactions. The probe is a third oligonucleotide primer which recognizes the target amplicon and is typically homologous to sequences between the main amplification primers. The use of fluorophore/quencher with probes in real-time detection formats is a very convenient way to monitor amplification events in RPA reactions.

RPA technology is compatible with a variety of different types of oligonucleotide probes. The structures of three types—Exo-probes, LF-probes, and Fpg-probes—are each discussed below.

Exo-Probes

Figure 2:
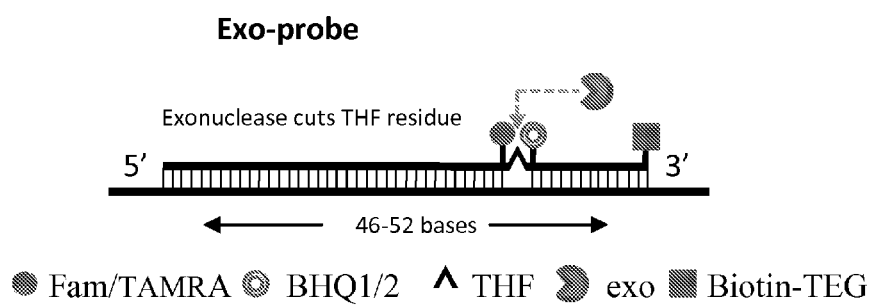
FIG. 2 depicts the structure of an annealed Exo-probe. The abasic THF residue is cleaved by exonuclease only when the probe is bound. Cleavage by exonuclease separates the fluorophore and quencher and generates fluorescent signal.

Exo-probes are generally 46-52 oligonucleotides long. Signal is generated by an internal dT fluorophore (Fluorescein or TAMRA) and quenched by an internal dT quencher (typically Black Hole Quencher (BHQ) 1 or 2) located 1-5 bases 3' to the fluorophore. In this case, probes are restricted to contain sequences where two thymines can be found with <6 intervening nucleotides. One of the bases between the fluorophore and quencher is the abasic nucleotide analog, tetrahydrofuran (THF—sometimes referred to as a 'dSpacer'). There should be at least 30 nucleotides placed 5' to the THF site, and at least a further 15 located 3' to it. When the probe has hybridized to the target sequence, Exonuclease III will recognize and cleave the THF, thereby separating the fluorophore and quencher and generating a fluorescent signal. The THF should be at least 31 bases from the 5' end of the probe and 16 bases from the 3' end. Finally, the probe is blocked from polymerase extension by a 3'-blocking group (e.g., Biotin-TEG). FIG. 2 depicts a typical annealed Exo-probe.

While there is no fixed rule describing the best position of a given probe relative to its corresponding amplification primers, care must be taken to avoid the possibility that primer artefacts can be detected by the probe. Although primers that have the same direction as the probe can even overlap its 5' part, this overlap must not extend up to the fluorophore/abasic-site/quencher portion of the probe (i.e., the overlap of the primer should be restricted to the 5'-most 27 nucleotides of the probe or so). This design will prevent the inadvertent generation of hybridization targets for the 'sensitive' sequence element of the probe by primer artefacts. Primers opposing the direction of the probe should not overlap to avoid the occurrence of primer-probe dimers.

LF-Probes

Figure 3:
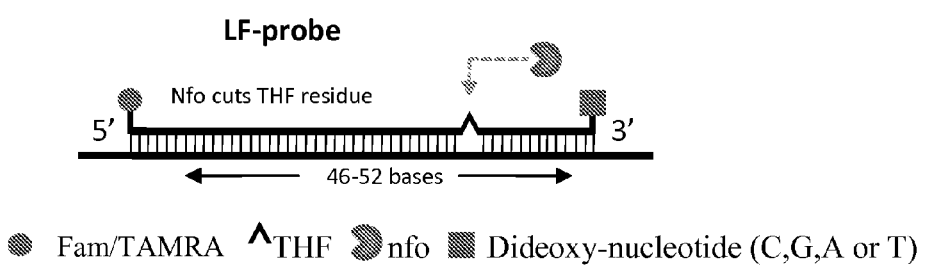
FIG. 3 depicts the structure of an annealed LF-probe. The abasic THF residue is cleaved by Nfo only when the probe is bound.

LF-probes are often 46-52 oligonucleotides long and intended for detection of RPA reactions in simple sandwich assays such as lateral flow strips. The probe is blocked from polymerase extension by making the last nucleotide a dideoxy nucleotide. As in an Exo-probe, a THF is typically positioned about 30 bases from the 5' end of the probe and 16 bases from the 3' end. When the probe has annealed to the target sequence, Nfo nuclease will recognize and cleave the THF. This allows the 5' portion of the cut probe to then act as a primer, ultimately leading to an amplicon containing the 5' portion of the probe conjoined to the opposing primer. The amplicon is detected by virtue of labels attached to the 5' end of the opposing primer (usually biotin) and to the 5' end of the probe (usually FAM). The duplex formed is captured on a surface coated with the appropriate capture molecule (e.g., streptavidin for biotin or an anti-FAM antibody for FAM). RPA products are run on lateral flow strips, such as available from Milenia Biotec. FIG. 3 depicts a typical annealed LF-probe.

While there is no fixed rule describing the best position of a given probe relative to its corresponding amplification primers, care must be taken to avoid the possibility that primer artefacts can be detected by the probe. Although primers that have the same direction as the probe can even overlap its 5' part, this overlap must not extend up to the abasic-site portion of the probe (i.e., the overlap of the primer should be restricted to the 5'-most 27 nucleotides of the probe or so). This design will prevent the inadvertent generation of hybridization targets for the 'sensitive' sequence element of the probe by primer artefacts. Primers opposing the direction of the probe should not overlap to avoid the occurrence of primer-probe dimers. The opposing amplification primer is usually labelled with biotin.

Fpg-Probes

Figure 4:
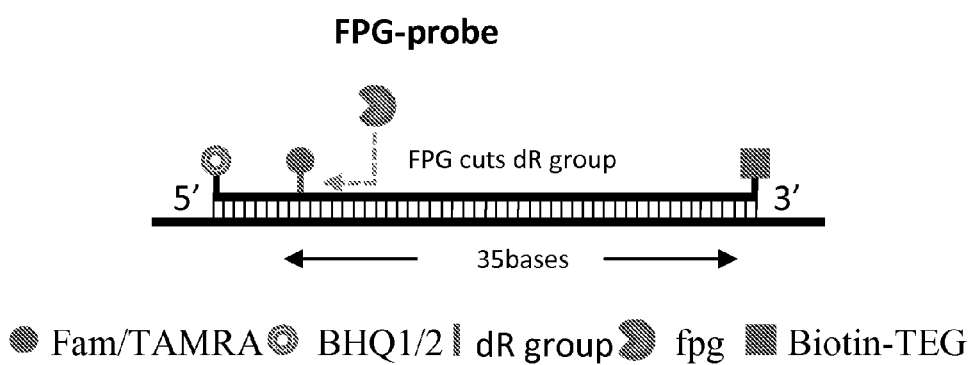
FIG. 4 depicts the structure of an annealed Fpg-probe. The abasic dR residue is cleaved by fpg only when the probe is bound. Cleavage by fpg releases the fluorophore from the probe and generates fluorescent signal.

Fpg-probes are generally 35 oligonucleotides long. At the 5' end of the probe is a quencher (typically Black Hole Quencher (BHQ) 1 or 2). Signal is generated by a fluorophore (typically FAM or Texas Red) attached to the ribose of a base-less nucleotide analog (a so-called dR residue; a fluorophore/O-linker effectively replaces the base at the C1 position of the ribose) 4-6 bases downstream of the 5' end. When the probe has annealed to the target sequence, fpg will recognize and cleave the dR, thereby releasing the fluorophore from the probe and generating a fluorescent signal. Finally, the probe is blocked from polymerase extension by a 3'-blocking group (e.g., Biotin-TEG). FIG. 4 is a schematic of a typical annealed Fpg-probe. FIG. 7 depicts the structure of an annealed Fpg-probe. The abasic dR residue is cleaved by fpg only when the probe is bound. This releases the fluorophore from the probe and generates fluorescent signal.

While there is no fixed rule describing the best position of a given Fpg-probe relative to the amplification primers with which it is used, care must be taken to avoid the possibility that primer artefacts can be detected by the probe. As a result any overlap between primers and the probe should be avoided.

Example 4

RPA Reaction with Real Time Monitoring Using Exonuclease III

A RPA reaction using exonuclease III is performed using a modified protocol of Example 2. Each sample is established by reconstituting the Exo RPA Freeze Dried Reaction Pellet of Example 1 with a suitable rehydration solution. The rehydration solution is prepared from the rehydration buffer of Example 1, amplification primers, template and an Exo-probe (and water to a total volume of 47.5 μL per sample). The reaction is initiated by the addition of 2.5 μL of a 280 mM Magnesium-Acetate solution, bringing the final reaction volume to 50 μL per sample.

For each sample, the rehydration solution is prepared by adding 2.4 μL of the first primer (10 μM), 2.4 μL of the second primer (10 μM), the Template and 0.6 μL of an Exo-probe (10 μM) as described in Example 3. $H_2O$ is added to bring the total volume of the foregoing components to 18 μt. 29.5 μL of the rehydration buffer of Example 1 is added. The rehydration solution is then vortexed and is spun briefly.

For each sample, the 47.5 μL of rehydration solution is transferred to an Exo RPA Freeze Dried Reaction Pellet of Example 1. The sample is mixed by pipetting up and down until the entire pellet has been resuspended. For each sample, 2.5 μL of 280 mM Magnesium-Acetate is added and is mixed well to initiate the reaction.

The tubes are place into a suitable thermal incubator/fluorometer (e.g., isothermally set to a temperature of 37-39° C.) and are incubated while fluorescence measurements are periodically taken. After 4 minutes, the samples are taken out of the incubator, vortexed, spun down and returned to the incubator/fluorometer. The total incubation/detection time is 20 minutes.

Example 5

RPA Reaction Using Nfo

A RPA reaction using Nfo is performed using a modified protocol of Example 2. Each sample is established by reconstituting the Nfo RPA Freeze Dried Reaction Pellet of Example 1 with a suitable rehydration solution. The rehydration solution is prepared from the rehydration buffer of Example 1, amplification primers, template and an LF-probe (and water to a total volume of 47.5 ηL per sample). The reaction is initiated by the addition of 2.5 μL of a 280 mM Magnesium-Acetate solution, bringing the final reaction volume to 50 μL per sample.

For each sample, the rehydration solution is prepared by adding 2.4 μL of the first primer (10 μM), 2.4 μL of the second primer (10 μM), the Template and 0.6 μL of an LF-probe (10 μM) as described in Example 3. $H_2O$ is added to bring the total volume of the foregoing components to 18 μL. 29.5 μL it of the rehydration buffer of Example 1 is added. The rehydration solution is then vortexed and is spun briefly.

For each sample, the 47.5 μL of rehydration solution is transferred to an Nfo RPA Freeze Dried Reaction Pellet of Example 1. The sample is mixed by pipetting up and down until the entire pellet has been resuspended. For each sample, 2.5 μL of 280 mM Magnesium-Acetate is added and is mixed well to initiate the reaction.

The tubes are place into a suitable incubator block (e.g., set to a temperature of 37-39° C.) and are incubated for 4 minutes. For ultra-high sensitivity after 4 minutes, the samples are taken out of the incubator, vortexed, spun down and returned to the incubator block. The total incubation time is 15-30 minutes. After the reaction is completed, the outcome of each reaction is typically analyzed by an endpoint method, such as a sandwich assay technique.

Example 6

RPA Reaction with Real Time Monitoring Using Fpg

A RPA reaction using fpg is performed using a modified protocol of Example 2. Each sample is established by reconstituting the Fpg RPA Freeze Dried Reaction Pellet of Example 1 with a suitable rehydration solution. The rehydration solution is prepared from the rehydration buffer of Example 1, amplification primers, template and an Fpg-probe (and water to a total volume of 47.5 μL per sample). The reaction is initiated by the addition of 2.5 μL of a 280 mM Magnesium-Acetate solution, bringing the final reaction volume to 50 μL per sample.

For each sample, the rehydration solution is prepared by adding 2.40 μL of the first primer (10 μM), 2.40 μL of the second primer (10 μM), the Template and 0.6 ηL of an Fpg-probe (10 μM) as described in Example 3. $H_2O$ is added to bring the total volume of the foregoing components to 18 μL. 29.5 μL of the rehydration buffer of Example 1 is added. The rehydration solution is then vortexed and is spun briefly.

For each sample, the 47.5 μL of rehydration solution is transferred to an Fpg RPA Freeze Dried Reaction Pellet of Example 1. The sample is mixed by pipetting up and down until the entire pellet has been resuspended. For each sample, 2.5 μL of 280 mM Magnesium-Acetate is added and is mixed well to initiate the reaction.

The tubes are place into a suitable thermal incubator/fluorometer (e.g., isothermally set to a temperature of 37-39° C.) and are incubated while fluorescence measurements are periodically taken. After 4 minutes, the samples are taken out of the incubator, vortexed, spun down and returned to the incubator/fluorometer. The total incubation/detection time is 20 minutes.

The details of one or more embodiments of the invention have been set forth in the accompanying description above. Although any methods and materials similar or equivalent to those described herein can be used in the practice or testing of the present invention, the preferred methods and materials are now described. Other features, objects, and advantages of the invention will be apparent from the description and from the claims.

In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. All sequence citations, patents, patent applications and publications cited in this specification are hereby incorporated by reference herein, including the disclosures provided by U.S. Pat. No. 7,270,981 filed Feb. 21, 2003; U.S. Pat. No. 7,399, 590 filed Sep. 1, 2004; U.S. Pat. No. 7,435,561 filed Jul. 25, 2006 and U.S. Pat. No. 7,485,428 filed Aug. 13, 2007, as well as, U.S. application Ser. No. 11/628,179, filed Aug. 30, 2007; Ser. No. 11/800,318 filed May 4, 2007 and 61/179,793 filed May 20, 2009.

What is claimed is:

1. A kit for a recombinase polymerase amplification process of DNA amplification of a target nucleic acid molecule comprising:
 (a) one or more freeze dried pellets each comprising the following reagents in the following concentrations, which-unless otherwise indicated can be the concentration either when reconstituted or when freeze dried;

(1) 1.5%-5% (weight/lyophilization mixture volume) of polyethylene glycol;
(2) 2.5%-7.5% weight/volume of trehalose;
(3) 0-60 mM Tris buffer;
(4) 1-10 mM DTT;
(5) 150-400 µM dNTPs;
(6) 1.5-3.5 mM ATP;
(7) 100-350 ng/µL uvsX recombinase;
(8) optionally 50-200 ng/µL uvsY;
(9) 150-800 ng/µL gp32;
(10) 30-150 ng/µL Bsu polymerase or Sau polymerase;
(11) 20-75 mM phosphocreatine; and
(12) 10-200 ng/µL creatine kinase.

2. The kit of claim 1, wherein each of the freeze dried reagents is in approximately the following concentrations, which unless otherwise indicated can be the concentration either when reconstituted or when freeze dried:
(1) 2.28% (weight/lyophilization mixture volume) of polyethylene glycol, wherein the polyethylene glycol has a molecular weight of 35 kilodaltons;
(2) 5.7% weight/volume of trehalose;
(3) 25 mM Tris buffer;
(4) 5 mM DTT;
(5) 240 µM dNTPs;
(6) 2.5 mM ATP;
(7) 260 ng/µL uvsX recombinase;
(8) 88 ng/µL uvsY;
(9) 254 ng/µL gp32;
(10) 90 ng/µL Sau polymerase;
(11) 50 mM phosphocreatine; and
(12) 100 ng/µL creatine kinase.

3. The kit according to either of claims 1 or 2, wherein said kit comprises 8 freeze dried pellets.

4. The kit according to either of claims 1 or 2, wherein said kit comprises 96 freeze dried pellets.

5. The kit according to any one of claims 1 or 2, further comprising:
(b) a rehydration buffer for reconstituting said freeze dried pellets, wherein said rehydration buffer comprises:
0-60 mM Tris buffer;
50-150 mM Potassium Acetate; and
0.3%-7.5% weight/volume of polyethylene glycol.

6. The kit according to claim 5, wherein said rehydration buffer comprises
25 mM Tris buffer;
approximately 100 mM Potassium Acetate; and
approximately 5.46% weight/volume of polyethylene glycol, wherein the polyethylene glycol has a molecular weight of 35 kilodaltons.

7. The kit according to claim 5, wherein said kit comprises 4 mL of said rehydration buffer.

8. The kit according to claim 5, wherein said rehydration buffer further comprises 8-16 mM Magnesium Acetate.

9. The kit according to claim 8, wherein said rehydration buffer comprises approximately 14 mM Magnesium Acetate.

10. The kit according to claim 5, further comprising:
(c) a 160-320 mM Magnesium Acetate solution.

11. The kit according to claim 10, where the concentration of said Magnesium Acetate solution is approximately 280 mM.

12. The kit according to claim 10, wherein said kit comprises 250 µL of said Magnesium Acetate solution.

13. The kit according to any one of claims 1 or 2, wherein said freeze dried pellets further comprise 50-1000 nM of a first primer and 50-1000 nM of a second primer.

14. The kit according to any one of claims 1 or 2, wherein said freeze dried pellets further comprises a nuclease.

15. The kit according to claim 14, wherein said kit further comprises a positive control, wherein said positive control comprises a positive control DNA, a first positive control nucleic acid primer, a second positive control nucleic acid primer and a positive control nucleic acid probe, and said probe is capable of being cleaved by said nuclease when said probe is hybridized to said positive control DNA.

16. The kit according to claim 15, wherein said positive control DNA comprises human genomic DNA, said first and second positive control nucleic acid primers are each provided at a concentration of about 10 µM and said positive control nucleic acid probe is provide at a concentration of about 120 nM.

17. The kit according to claim 14, wherein said nuclease is selected from the group consisting of exonuclease III (exoIII), endonuclease IV (Nfo) and 8-oxoguanine DNA glycosylase (fpg).

18. The kit according to claim 17, wherein said pellets comprise 50-200 ng/µL of said nuclease.

19. The kit according to claim 18, wherein said pellets comprise approximately 96 ng/µL exoIII.

20. The kit according to claim 18, wherein said pellets comprise approximately 62 ng/µL Nfo.

21. The kit according to claim 18, wherein said pellets comprise approximately 114 ng/µL fpg.

22. A recombinase polymerase amplification process of DNA amplification comprising the steps of:
(a) combining the following reagents in a solution in the absence of Magnesium:
(1) at least one recombinase;
(2) at least one single stranded DNA binding protein;
(3) at least one DNA polymerase;
(4) dNTPs;
(5) polyethylene glycol;
(6) a buffer;
(7) a reducing agent;
(8) ATP;
(9) optionally at least one recombinase loading protein;
(10) a first primer and a second primer; and
(11) a target nucleic acid molecule;
(b) adding Magnesium to initiate the amplification reaction; and
(c) incubating said solution until a desired degree of amplification is achieved.

23. The process of claim 22, wherein one or more of the reagents of step (a) are freeze dried before step (a).

24. The process of claim 23, wherein step (c) comprises the following steps:
(1) incubating said solution for a first period of time;
(2) mixing said solution; and
(3) incubating said solution for a second period of time until the desired degree of amplification is achieved.

25. The process of claim 24, wherein said first period of time is about four minutes.

26. The process of claim 24, wherein said mixing step comprises vortexing said solution.

27. The process of claim 22, wherein the Magnesium is added in the form of a Magnesium Acetate solution.

28. The process of claim 22, wherein the Magnesium is added to a final concentration of 8-16 mM.

29. The process of claim 28, wherein the Magnesium is added to a final concentration of about 14 mM.

30. A recombinase polymerase amplification process of DNA amplification comprising the steps of:
(a) providing the kit of claim 5;
(b) reconstituting at least one of said freeze dried pellets with the following in any order:

(1) said rehydration buffer;
(2) a first nucleic acid primer and a second nucleic acid primer; a
(3) a target nucleic acid; and
(4) optionally water;
(c) adding Magnesium to initiate the amplification reaction; and
(d) incubating said reaction until a desired degree of amplification is achieved.

31. The process of claim 30, wherein the Magnesium is added in the form of a Magnesium Acetate solution.

32. The process of claim 30, wherein the Magnesium is added to a final concentration of 8-16 mM.

33. The process of claim 32, wherein the Magnesium is added to a final concentration of about 14 mM.

34. The process of claim 30, wherein said freeze dried pellet comprises a nuclease and wherein said freeze dried is also reconstituted with a nucleic acid probe, where said probe is capable of being cleaved by said nuclease when said probe is hybridized to said target nucleic acid.

35. The process of claim 30, wherein a plurality of freeze dried pellets are reconstituted during step (b) and initiating each amplification reaction simultaneously by adding the Magnesium to each reconstituted pellet at the same time during step (c).

36. The process of claim 30, wherein the reaction volume after step (c) is approximately 50 µL.

37. The process of claim 30, wherein step (d) comprises the following steps:
(1) incubating said solution for a first period of time;
(2) mixing said solution; and
(3) incubating said solution for a second period of time until the desired degree of amplification is achieved.

38. The process of claim 37, wherein said first period of time is about four minutes.

39. The process of claim 37, wherein said mixing step comprises vortexing said solution.

40. The kit according to claim 3, further comprising:
(b) a rehydration buffer for reconstituting said freeze dried pellets, wherein said rehydration buffer comprises:
0-60 mM Tris buffer;
50-150 mM Potassium Acetate; and
0.3%-7.5% weight/volume of polyethylene glycol.

41. The kit according to claim 4, further comprising:
(b) a rehydration buffer for reconstituting said freeze dried pellets, wherein said rehydration buffer comprises:
0-60 mM Tris buffer;
50-150 mM Potassium Acetate; and
0.3%-7.5% weight/volume of polyethylene glycol.

* * * * *

UNITED STATES PATENT AND TRADEMARK OFFICE
CERTIFICATE OF CORRECTION

PATENT NO. : 9,057,097 B2  
APPLICATION NO. : 13/375264  
DATED : June 16, 2015  
INVENTOR(S) : Piepenburg et al.

Page 1 of 1

It is certified that error appears in the above-identified patent and that said Letters Patent is hereby corrected as shown below:

In the Claims
Col. 17, line 3, in claim 30, after "primer;" delete "a"

Signed and Sealed this
Seventeenth Day of November, 2015

Michelle K. Lee
*Director of the United States Patent and Trademark Office*